US012807612B2

(12) United States Patent
Medendorp et al.

(10) Patent No.: US 12,807,612 B2
(45) Date of Patent: Nov. 24, 2026

(54) SALT AND CRYSTAL FORMS OF AN ACTIVIN RECEPTOR-LIKE KINASE INHIBITOR

(71) Applicant: Blueprint Medicines Corporation, Cambridge, MA (US)

(72) Inventors: Clare Medendorp, Cambridge, MA (US); Debra Mazaik, Cambridge, MA (US); Gordon Wilkie, Cambridge, MA (US); Joshua D. Waetzig, Cambridge, MA (US); Brian Heinrich, Cambridge, MA (US); Lauren MacEachern, Dartmouth (CA); Dominik Siegel, Dottikon (CH); Harald Ohmer, Dottikon (CH); Steven C. Johnston, Woburn, MA (US)

(73) Assignee: Blueprint Medicines Corporation, Cambridge, MA (US)

( * ) Notice: Subject to any disclaimer, the term of this patent is extended or adjusted under 35 U.S.C. 154(b) by 1328 days.

(21) Appl. No.: 17/633,440

(22) PCT Filed: Aug. 12, 2020

(86) PCT No.: PCT/US2020/045847

§ 371 (c)(1),
(2) Date: Feb. 7, 2022

(87) PCT Pub. No.: WO2021/030386

PCT Pub. Date: Feb. 18, 2021

(65) Prior Publication Data

US 2022/0281879 A1 Sep. 8, 2022

Related U.S. Application Data

(60) Provisional application No. 62/885,977, filed on Aug. 13, 2019.

(51) Int. Cl.
*C07D 487/04* (2006.01)

(52) U.S. Cl.
CPC ........ *C07D 487/04* (2013.01); *C07B 2200/13* (2013.01)

(58) Field of Classification Search
CPC .......................... C07D 487/04; C07B 2200/13
See application file for complete search history.

(56) References Cited

U.S. PATENT DOCUMENTS

| | | | |
|---|---|---|---|
| 7,960,551 B2 | 6/2011 | Chudasama et al. | |
| 8,674,105 B2 | 3/2014 | Avalle et al. | |
| 10,233,186 B2 * | 3/2019 | Brooijmans ......... | C07D 487/04 |

FOREIGN PATENT DOCUMENTS

| | | |
|---|---|---|
| JP | 2019-513781 A | 5/2019 |
| WO | 2014/138088 A1 | 9/2014 |
| WO | 2017/181117 A1 | 10/2017 |
| WO | 2018/200855 A1 | 11/2018 |
| WO | 2018/232094 A1 | 12/2018 |

OTHER PUBLICATIONS

Kazuhide, Physico-Chemical Studies on the Molecular Details of Drug Crystals. Pharm Tech Japan. Sep. 2002;18(10):81-96.
Japanese Office Action for Application No. 2022-508779, dated Aug. 5, 2024, 9 pages.
Brittain, Polymorphism in Pharmaceutical Solids. Marcel Kekker, Inc., New York. pp. 1-2, 125-181, 183-226, (1999).
Berge et al., Pharmaceutical salts. J Pharm Sci. Jan. 1977;66(1):1-19.
Kumar et al., An overview of automated systems relevant in pharmaceutical salt screening. Drug Discov Today. Dec. 2007;12(23-24):1046-53.
International Search Report and Written Opinion for Application No. PCT/US2020/045847, dated Nov. 18, 2020, 13 pages.
Bastin et al., Salt Selection and Optimisation Procedureds for Pharmaceutical New Chemical Entities. Organic Process Research & Development. 2000;4:427-435.
Kummerer, Pharmaceuticals in the Environment. Annu Rev Environ Resour. 2010;35:57-75.

(Continued)

*Primary Examiner* — Adam C Milligan
*Assistant Examiner* — William Y Lee
(74) *Attorney, Agent, or Firm* — McCarter & English, LLP; Wei Song

(57) ABSTRACT

Various salt forms of Compound (I) represented by the following structural formula, and their corresponding pharmaceutical compositions, are disclosed. Particular single crystalline forms of 1:1.5 Compound (I) succinate, 1:1 Compound (I) hydrochloride salt, and 1:1 Compound (I) fumarate salt are characterized by a variety of properties and physical measurements. Methods of preparing specific crystalline forms are also disclosed. The present disclosure also provides methods of treating or ameliorating fibrodysplasia ossificans progressive in a subject.

(I)

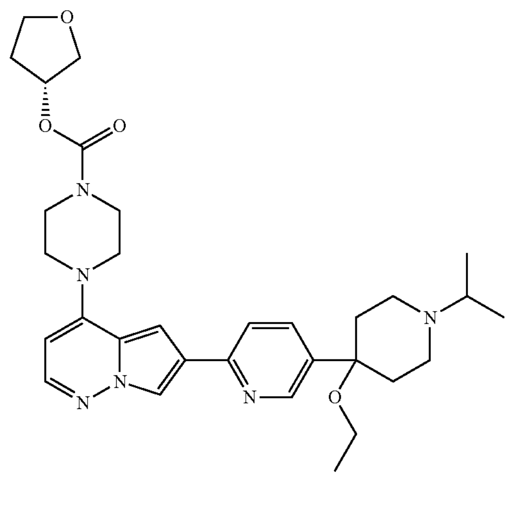

21 Claims, 30 Drawing Sheets

(56) References Cited

OTHER PUBLICATIONS

Sarma et al., Solid forms of pharmaceuticals: Polymorphs, salts and cocrystals. Korean J Chem Eng. 2011;28(2):315-322.
Thakuria et al., Pharmaceutical cocrystals and poorly soluble drugs. Int J Pharm. Aug. 30, 2013;453(1):101-25.
Variankaval et al., From Form to Function: Crystallization of Active Pharmaceutical Ingredients. AlChE Journal. Jul. 2008;54(7):1682-1688.
Bavin, Polymorphism in Process Development. Chemistry & Industry. Aug. 21, 1989;527-529.
Byrn et al., Pharmaceutical solids: a strategic approach to regulatory considerations. Pharm Res. Jul. 1995; 12(7):945-54.
Carlson et al., An integrated high throughput workflow for preformulations: Polymorph and salt selection studies. Drug Development. Jul./Aug 2023, pp. 10-15.

* cited by examiner

SALT AND CRYSTAL FORMS OF AN ACTIVIN RECEPTOR-LIKE KINASE INHIBITOR

CROSS-REFERENCE TO RELATED APPLICATIONS

This application is a 35 U.S.C. § 371 national stage filing of International Application No. PCT/US2020/045847, filed on Aug. 12, 2020, which claims priority from U.S. Provisional Application No. 62/885,977, filed Aug. 13, 2019. The entire contents of the aforementioned application are incorporated herein by reference.

BACKGROUND

Activin receptor-like kinase-2 (ALK2) is encoded by the Activin A receptor, type I gene (ACVR1). ALK2 is a serine/threonine kinase in the bone morphogenetic protein (BMP) pathway (Shore et al., Nature Genetics 2006, 38: 525-27). Inhibitors of ALK2 and mutant forms of ALK2 have the potential to treat a number of diseases, including fibrodysplasia ossificans progressiva (FOP); heterotopic ossification (HO) induced by, for example, major surgical interventions, trauma (such as head or blast injuries), protracted immobilization, or severe burns; diffuse intrinsic pontine glioma (DIPG), a rare form of brain cancer; and anemia associated with chronic inflammatory, infectious or neoplastic disease.

U.S. Pat. No. 10,233,186, the entire teachings of which are incorporated herein by reference, discloses potent, highly selective inhibitors of ALK2 and mutant forms of ALK2. The structure of one of the inhibitors disclosed in U.S. Pat. No. 10,233,186, referred to herein as "Compound (I)" is shown below:

Compound (I)

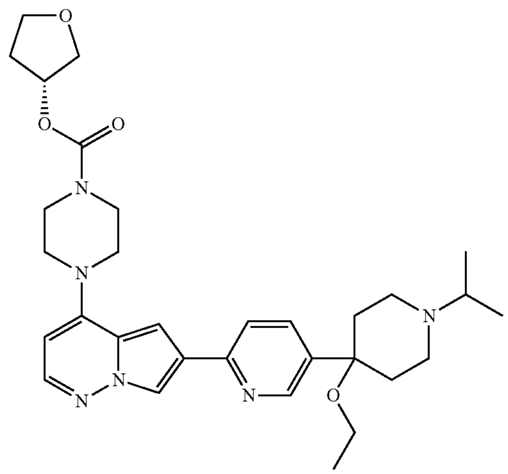

The successful development of pharmaceutically active agents, such as Compound (I), typically requires the identification of a solid form with properties that enable ready isolation and purification following synthesis, that are amendable to large scale manufacture, that can be stored for extended periods of time with minimal absorption of water, decomposition or transformation into other solid forms, that are suitable for formulation and that can be readily absorbed following administration to the subject (e.g., are soluble in water and in gastric fluids).

SUMMARY

It has now been found that the free base of Compound (I) is physically unstable in humid environments and tends to gum when exposed to water. As a consequence, Compound (I) was found to be difficult to isolate when prepared on a production scale.

It has now also been found that the 1.5:1 succinic acid salt (i.e., Sesqui-Succinate salt), the 1:1 hydrochloric acid salt (1:1 hydrochloride salt), and the 1:1 fumaric acid salt (1:1 fumarate salt) can be crystallized under well-defined conditions to provide non-hygroscopic crystalline forms (see Examples 2-7). These three salts also have good solubility in water and in simulated gastric fluids (see Table 2), have high melting point onsets and are suitable for large scale synthesis. The 1.5:1 succinic acid salt has the additional advantage that it exists as a single polymorph and undergoes no thermal transitions below its melting point, indicating a high degree of form stability (see Example 2.4). The designation "1:1" is the molar ratio between acid (hydrochloric acid or fumaric acid) and Compound (I); and the designation "1.5:1" is the molar ratio between acid (succinic acid) and Compound (I). Because of the two carboxylic acid groups on succinic acid and the three basic nitrogen atoms in Compound (I), multiple possible stoichiometries are possible. For example, Compound (I) forms both a 1:1 hydrochloric acid salt and a 2:1 hydrochloric acid salt. The 1:1 hydrochloric acid salt of Compound (I) is referred to herein as "1:1 Compound (I) HCl"; and the 1.5:1 succinic acid salt is referred to herein as "1.5:1 Compound (I) Sesqui-Succinate".

Compound (I) HCl, Compound (I) fumarate and Compound (I) Sesqui-Succinate were identified from a salt screening with thirteen different acids (see Example 1). From this salt screen, only eight crystalline forms were identified. Crystalline salts were formed with benzenesulfonic acid, benzoic acid, fumaric acid, HCl (1 and 2 molar equivalents), maleic acid, salicylic acid, and succinic acid. From these eight salts, the besylate, maleate, and 2:1 HCl were found to be unsuitable due to low crystallinity and instability in a humid environment (deliquescence); the benzoate was found to be unsuitable due to poor water solubility and high mass loss on melting; and the salicylate was found to be unsuitable due to poor water solubility, high mass loss on melting, and possibly being polymorphic.

In one aspect, the present disclosure provides a succinate salt of Compound (I) wherein the molar ratio between Compound (I) and succinic acid is 1:1.5. As noted above, this salt is also referred to herein as "1.5:1 Compound (I) Sesqui-Succinate".

In another aspect, the present disclosure provides a HCl salt of Compound (I) wherein the molar ratio between Compound (I) and HCl acid is 1:1. As noted above, this salt is also referred to herein as "1:1 Compound (I) HCl Salt".

In yet another aspect, the present disclosure provides a fumarate salt of Compound (I) wherein the molar ratio between Compound (I) and fumaric acid is 1:1. This salt is also referred to herein as "1:1 Compound (I) Fumarate Salt".

In another aspect, the present disclosure provides a pharmaceutical composition comprising 1.5:1 Compound (I) Sesqui-Succinate (or 1:1 Compound (I) HCl Salt or 1:1 Compound (I) Fumarate Salt) and a pharmaceutically acceptable carrier or diluent.

The present disclosure provides a method of treating or ameliorating fibrodysplasia ossificans progressiva in a subject, comprising administering to the subject in need thereof a pharmaceutically effective amount of the salt of disclosed herein or the corresponding pharmaceutical composition.

The present disclosure provides a method of treating or ameliorating diffuse intrinsic pontine glioma in a subject, comprising administering to the subject in need thereof a pharmaceutically effective amount of the salt of disclosed herein or the corresponding pharmaceutical composition.

The present disclosure also provides a method of inhibiting aberrant ALK2 activity in a subject, comprising administering to the subject in need thereof a pharmaceutically effective amount of the salt of disclosed herein or the corresponding pharmaceutical composition.

The present disclosure also provides a use of the salt of the disclosure or a pharmaceutical composition thereof comprising the same in any of the methods of the disclosure described above. In one embodiment, provided is the salt of the disclosure or a pharmaceutical composition thereof comprising the same for use in any of the method of the disclosure described herein. In another embodiment, provided is use of the salt of the disclosure or a pharmaceutical composition thereof comprising the same for the manufacture of a medicament for any of the method of the disclosure described.

DETAILED DESCRIPTION

The present disclosure is directed to a novel succinate salt (i.e., 1:1.5 Sesqui-Succinate salt) of Compound (I), a novel hydrochloric acid salt (i.e., 1:1 hydrochloride salt) of Compound (I) and a novel fumaric acid salt (i.e., 1:1 fumarate salt) as well as polymorphic forms of each of the foregoing.

"Hydrated form" refers to a solid or a crystalline form of Compound (I) in free base or a salt where water is combined with free base Compound (I) or the corresponding salt in a stoichiometric ratio (e.g., a molar ratio of Compound (I): water 1:1 or 1:2) as an integral part of the solid or a crystal. "Unhydrated form" refers to a form which has no stoichiometric ratio between water and the free base of Compound (I) or the corresponding salt of Compound (I), and water is not substantially (e.g., less that 10% by weight by Karl Fischer analysis) present in the solid form. The new solid forms disclosed in the present disclosure include hydrated forms and unhydrated forms.

As used herein, "crystalline" refers to a solid having a crystal structure wherein the individual molecules have a highly homogeneous regular three dimensional configuration.

The disclosed crystalline Compound (I) salts can be crystals of a single crystal form or a mixture of crystals of different single crystalline forms. A single crystal form means the Compound (I) is a single crystal or a plurality of crystals in which each crystal has the same crystal form.

For the crystalline forms of Compound (I) disclosed herein, at least a particular percentage by weight of 1.5:1 Compound (I) salt is in a single crystal form. Particular weight percentages include 85%, 86%, 87%, 88%, 89%, 90%, 91%, 92%, 93%, 94%, 95%, 96%, 97%, 98%, 99%, 99.5%, 99.9%, or a weight percentage of 70%-75%, 75%-80%, 80%-85%, 85%-90%, 90%-95%, 95%-100%, 70-80%, 80-90%, 90-100% by weight of the Compound (I) salt is in a single crystal form. It is to be understood that all values and ranges between these values and ranges are meant to be encompassed by the present disclosure.

When the crystalline Compound (I) salt is defined as a specified percentage of one particular crystal form of the Compound (I) salt, the remainder is made up of amorphous form and/or crystal forms other than the one or more particular forms that are specified. Examples of single crystal forms include 1.5:1 Compound (I) Sesqui-Succinate (Form A), the 1:1 Compound (I) HCl salt (Forms A, D, G and I) and Compound (I) 1:1 fumarate (Forms A, C and D) characterized by one or more properties as discussed herein.

Compound (I) has a chiral center. Compound (I) in the salts and polymorphs disclosed herein is at least 80%, 90%, 99% or 99.9% by weight pure relative to the other stereoisomers, i.e., the ratio of the weight of the stereoisomer over the weight of all the stereoisomers.

Figure 1:
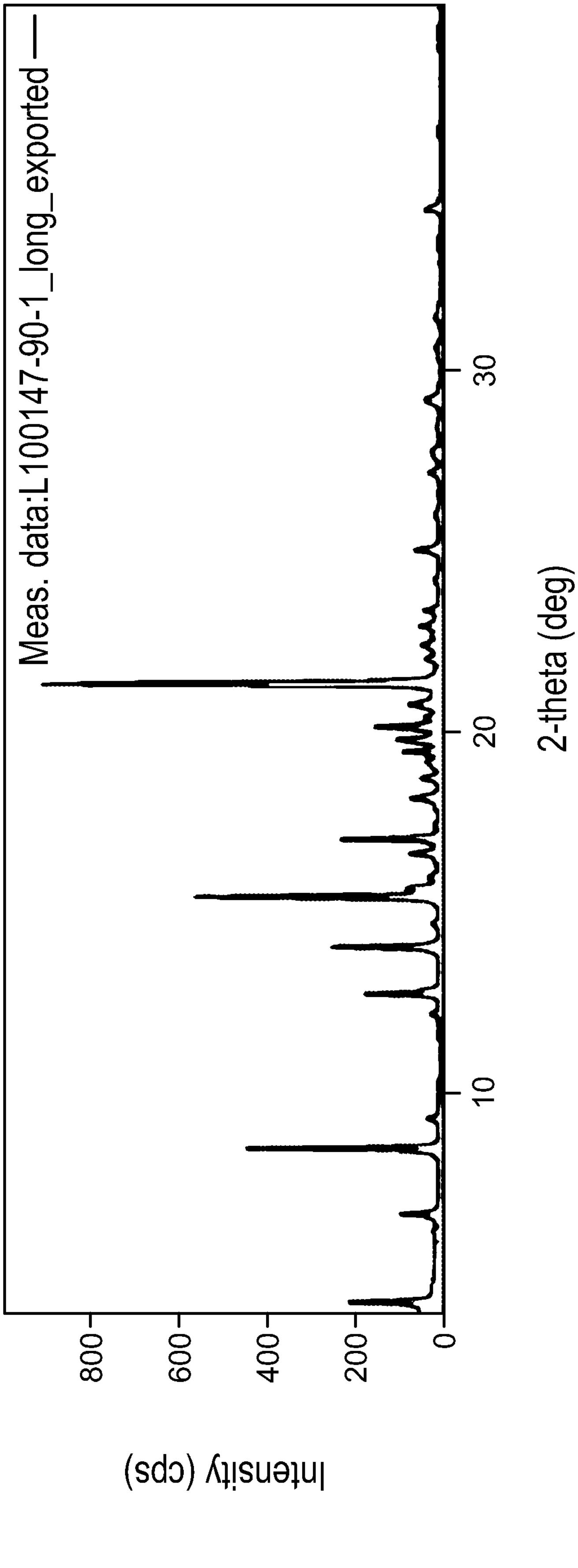
FIG. 1 shows the X-ray Powder Diffraction (XRPD) pattern of 1.5:1 Compound (I) Sesqui-Succinate.

The crystalline Compound (I) salts disclosed herein exhibit strong, unique XRPD patterns with sharp peaks corresponding to angular peak positions in 2θ and a flat baseline, indicative of a highly crystalline material (e.g., see FIG. 1). The XRPD patterns disclosed in the present application are obtained from a copper radiation source (Cu Kα1; λ=1.5406 A).

Characterization of 1.5:1 Compound (I) Sesqui-Succinate Crystalline Forms

In one embodiment, 1.5:1 Compound (I) Sesqui-Succinate is a single crystalline form, Form A, characterized by an X-ray powder diffraction pattern which comprises peaks at 8.5°, 15.4°, and 21.3°±0.2 in 2θ. In another embodiment, Form A is characterized by an X-ray powder diffraction pattern which comprises at least three peaks (or four peaks) chosen from 4.3°, 8.5°, 14.0°, 15.4°, and 21.3°±0.2 in 2θ. In another embodiment, Form A is characterized by an X-ray powder diffraction pattern which comprises peaks at 4.3°, 8.5°, 14.0°, 15.4°, and 21.3°±0.2 in 2θ. In yet another embodiment, Form A is characterized by an X-ray powder diffraction pattern which comprises peaks at 4.3°, 6.7°, 8.5°, 12.8°, 14.0°, 15.4°, 17.0°, and 21.3°±0.2 in 2θ. In yet another embodiment, Form A is characterized by an X-ray powder diffraction pattern which comprises peaks at 4.3°, 6.7°, 8.5°, 12.8°, 14.0°, 15.4°, 15.7°, 16.6°, 17.0°, 18.1°, 19.4°, 19.8°, 20.1°, 20.7°, 21.3°, 22.3°, 25.0°, 29.1°, and 34.4°±0.2 in 2θ. In yet another embodiment, Form A is characterized by an X-ray powder diffraction pattern substantially similar to FIG. 1.

It is well known in the crystallography art that, for any given crystal form, an angular peak position may vary slightly due to factors such as temperature variation, sample displacement, and the presence or absence of an internal standard. In the present disclosure, the variability of an angular peak position is ±0.2 in 2θ. In addition, the relative peak intensities for a given crystal form may vary due to differences in crystallite sizes and non-random crystallite orientations in sample preparation for XRPD analysis. It is well known in the art that this variability will account for the above factors without hindering the unequivocal identification of a crystal form.

In another embodiment, 1.5:1 Compound (I) Sesqui-Succinate Form A is characterized by differential scanning calorimeter (DSC) peak phase transition temperatures of 177±2° C.

Characterization of 1:1 Compound (I) Hydrochloride Salt Crystalline Forms

In one embodiment, Form A is characterized by an X-ray powder diffraction pattern which comprises at least three peaks (or four peaks) chosen from 12.9°, 17.0°, 19.0°, 21.1°, and 22.8°±0.2 in 2θ. In another embodiment, 1:1 Compound (I) hydrochloride salt is a single crystalline form, Form A, characterized by an X-ray powder diffraction pattern which comprises peaks at 12.9°, 17.0°, 19.0°, 21.1°, and 22.8°±0.2 in 2θ. In another embodiment, Form A is characterized by an X-ray powder diffraction pattern which comprises peaks at 12.9°, 13.8°, 15.1°, 17.0°, 19.0°, 19.6°, 21.1°, and 22.8°±0.2 in 2θ. In yet another embodiment, Form A is characterized by an X-ray powder diffraction pattern which comprises peaks at 5.7°, 10.1°, 12.6°, 12.9°, 13.8°, 15.1°, 17.0°, 19.0°, 19.6°, 20.3°, 21.1°, 22.1°, 22.8°, 23.4°, 24.0°, 24.8°, 25.5°, 26.1°, and 28.6°±0.2 in 2θ. In yet another embodiment, Form A is characterized by an X-ray powder diffraction pattern substantially similar to FIG. 8.

In another embodiment, 1:1 Compound (I) hydrochloride salt Form A is characterized by differential scanning calorimeter (DSC) peak phase transition temperatures of 207±2° C.

In one embodiment, 1:1 Compound (I) hydrochloride salt is a single crystalline form, Form D, characterized by an X-ray powder diffraction pattern which comprises at least three peaks (or four peaks) chosen from 10.8°, 16.9°, 18.8°, 22.1°, and 24.7°±0.2 in 2θ. In another embodiment, 1:1 Compound (I) hydrochloride salt is a single crystalline form, Form D, characterized by an X-ray powder diffraction pattern which comprises peaks at 10.8°, 16.9°, 18.8°, 22.1°, and 24.7°±0.2 in 2θ. In another embodiment, Form D is characterized by an X-ray powder diffraction pattern which comprises peaks at 10.8°, 13.3°, 16.9°, 18.8°, 22.1°, and 24.7°±0.2 in 2θ. In yet another embodiment, Form D is characterized by an X-ray powder diffraction pattern which comprises peaks at 10.8°, 13.1°, 13.3°, 16.6°, 16.9°, 17.4°, 18.8°, 20.8°, 22.1°, and 24.7°±0.2 in 2θ. In yet another embodiment, Form D is characterized by an X-ray powder diffraction pattern substantially similar to FIG. 15.

In another embodiment, 1:1 Compound (I) hydrochloride salt Form D is characterized by differential scanning calorimeter (DSC) peak phase transition temperatures of 207±2° C.

In one embodiment, 1:1 Compound (I) hydrochloride salt is a single crystalline form, Form G, characterized by an X-ray powder diffraction pattern which comprises at least three peaks (or four peaks) chosen from 10.2°, 12.8°, 16.7°, 17.4°, 18.4°, and 22.5°±0.2 in 2θ. In another embodiment, 1:1 Compound (I) hydrochloride salt is a single crystalline form, Form G, characterized by an X-ray powder diffraction pattern which comprises peaks at 10.2°, 12.8°, 16.7°, 17.4°, 18.4°, and 22.5°±0.2 in 2θ. In another embodiment, Form G is characterized by an X-ray powder diffraction pattern which comprises peaks at 10.2°, 12.8°, 16.7°, 17.4°, 18.4°, 21.3°, 22.0°, 22.5°, and 24.3°±0.2 in 2θ. In yet another embodiment, Form G is characterized by an X-ray powder diffraction pattern which comprises peaks at 10.2°, 12.8°, 14.9°, 16.7°, 17.4°, 18.4°, 20.5°, 21.3°, 22.0°, 22.5°, and 24.3°±0.2 in 2θ. In yet another embodiment, Form D is characterized by an X-ray powder diffraction pattern substantially similar to FIG. 18.

In another embodiment, 1:1 Compound (I) hydrochloride salt Form G is characterized by differential scanning calorimeter (DSC) peak phase transition temperatures of 175±4° C. and 197±4° C.

In one embodiment, 1:1 Compound (I) hydrochloride salt is a single crystalline form, Form I, characterized by an X-ray powder diffraction pattern which comprises at least three peaks (or four peaks) chosen from 5.4°, 8.2°, 16.3°, 16.5°, 18.4°, and 21.5°±0.2 in 2θ. In another embodiment, 1:1 Compound (I) hydrochloride salt is a single crystalline form, Form I, characterized by an X-ray powder diffraction pattern which comprises peaks at 5.4°, 8.2°, 16.3°, 16.5°, 18.4°, and 21.5°±0.2 in 2θ. In another embodiment, Form I is characterized by an X-ray powder diffraction pattern which comprises peaks at 5.4°, 8.2°, 13.1°, 16.3°, 16.5°, 18.4°, and 21.5°±0.2 in 2θ. In yet another embodiment, Form I is characterized by an X-ray powder diffraction pattern which comprises peaks at 5.4°, 8.2°, 10.2°, 13.1°, 16.3°, 16.5°, 17.1°, 18.4°, 21.5°, and 21.8°±0.2 in 2θ. In yet another embodiment, Form I is characterized by an X-ray powder diffraction pattern substantially similar to FIG. 21.

In another embodiment, 1:1 Compound (I) hydrochloride salt Form I is characterized by differential scanning calorimeter (DSC) peak phase transition temperatures of 187±4° C. and 200±4° C.

Characterization of 2:1 Compound (I) Hydrochloride Salt Crystalline Form

Figure 25:
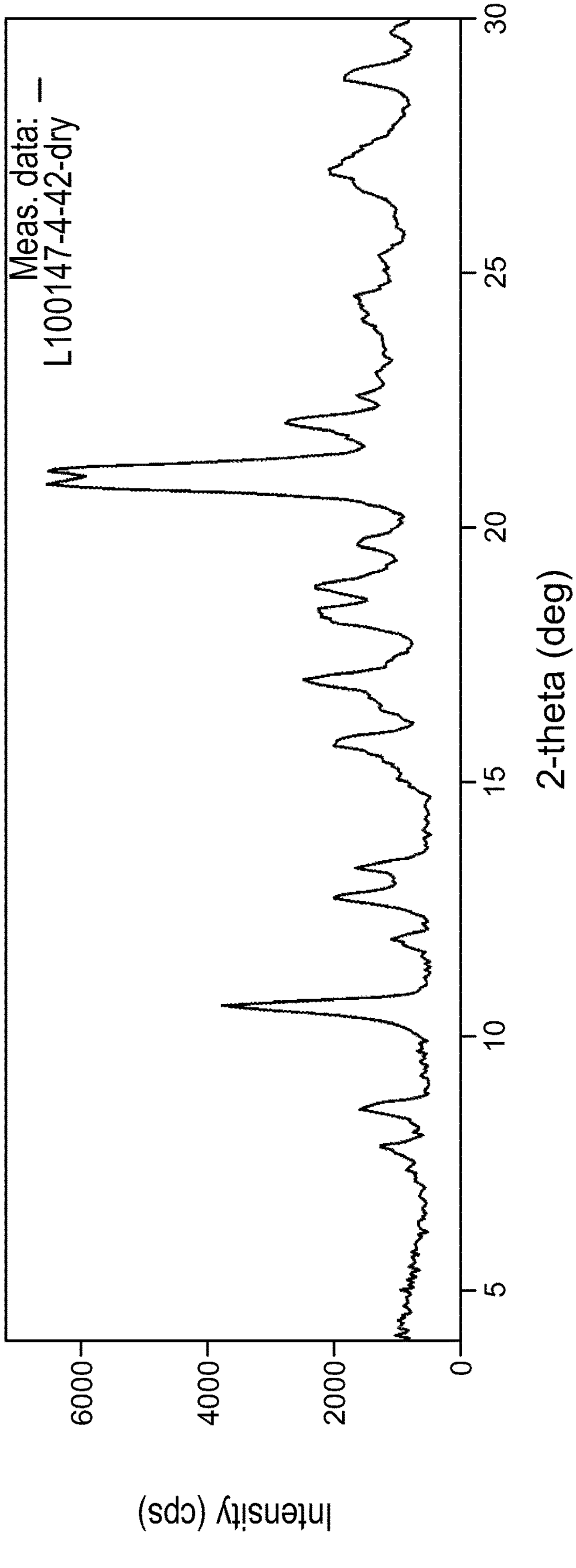
FIG. 25 shows the XRPD pattern of 2:1 Compound (I) crystalline HCl salt (Form B).

In one embodiment, 2:1 Compound (I) hydrochloride salt is a single crystalline form, Form B, characterized by an X-ray powder diffraction pattern which comprises at least three peaks (or four peaks) chosen from 10.6°, 17.0°, 18.3°, 20.9°, and 21.1°±0.2 in 2θ. In one embodiment, 2:1 Compound (I) hydrochloride salt is a single crystalline form, Form B, characterized by an X-ray powder diffraction pattern which comprises peaks at 10.6°, 17.0°, 18.3°, 20.9°, and 21.1°±0.2 in 2θ. In another embodiment, 2:1 Compound (I) hydrochloride salt Form B is characterized by an X-ray powder diffraction pattern which comprises peaks at 10.6°, 12.7°, 15.8°, 17.0°, 18.3°, 18.9°, 20.9°, 21.1°, and 22.0°±0.2 in 2θ. In yet another embodiment, 2:1 Compound (I) hydrochloride salt Form B is characterized by an X-ray powder diffraction pattern which comprises peaks at 7.8°, 8.6°, 10.6°, 11.9°, 12.7°, 13.3°, 15.4°, 15.8°, 16.5°, 17.0°, 18.3°, 18.9°, 19.7°, 20.9°, 21.1°, 22.0°, 22.6°, 24.5°, 26.7°, 27.1°, 28.9°, and 29.7°±0.2 in 2θ. In yet another embodiment, 2:1 Compound (I) hydrochloride salt Form B is characterized by an X-ray powder diffraction pattern substantially similar to FIG. 25.

Characterization of 1:1 Compound (I) Fumarate Crystalline Forms

Figure 26:
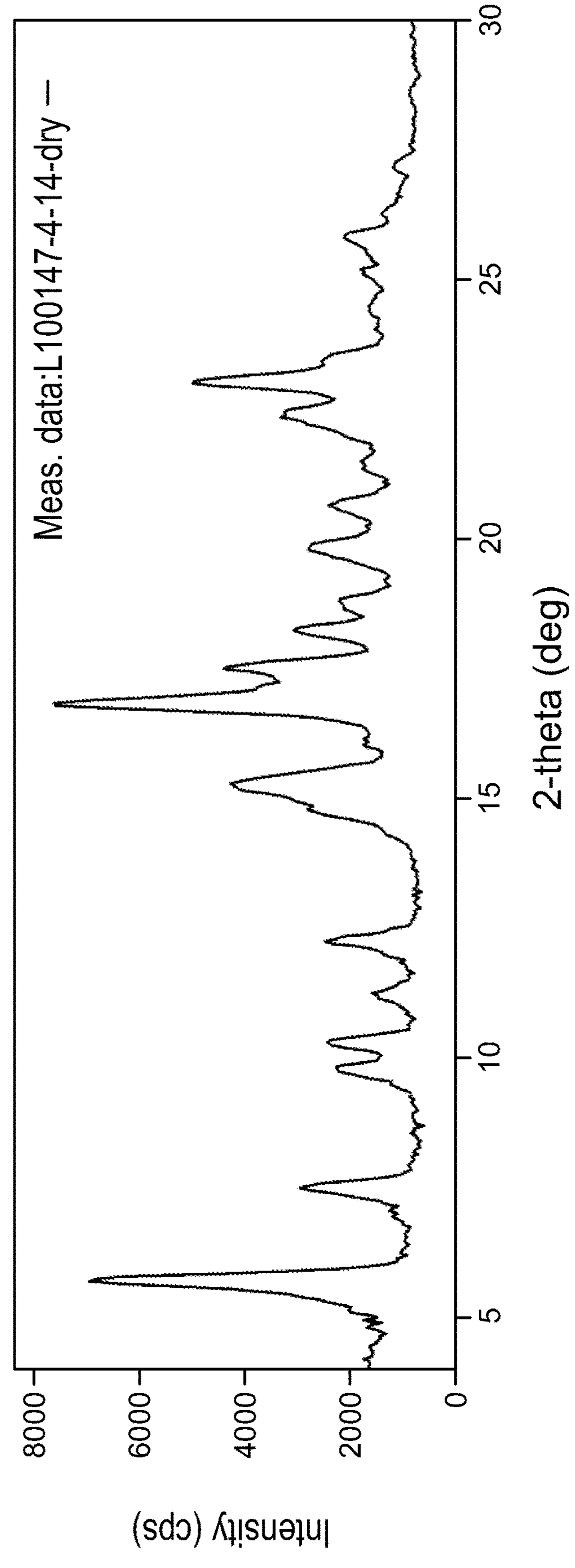
FIG. 26 shows the XRPD patterns of anhydrous 1:1 Compound (I) crystalline Fumarate salt (Form A) observed during initial screening (bottom) and scaled-up (top).

In one embodiment, 1:1 Compound (I) fumarate is a single crystalline form, Form A, characterized by an X-ray powder diffraction pattern which comprises at least three peaks (or four peaks) chosen from 5.7°, 15.3°, 16.9°, 22.4°, and 23.0°±0.2 in 2θ. In one embodiment, 1:1 Compound (I) fumarate is a single crystalline form, Form A, characterized by an X-ray powder diffraction pattern which comprises peaks at 5.7°, 15.3°, 16.9°, 22.4°, and 23.0°±0.2 in 2θ. In another embodiment, Form A is characterized by an X-ray powder diffraction pattern which comprises peaks at 5.7°, 7.5°, 9.8°, 10.3°, 12.3°, 15.3°, 16.9°, 17.5°, 22.4°, and 23.0°±0.2 in 2θ. In yet another embodiment, Form A is characterized by an X-ray powder diffraction pattern which comprises peaks at 5.7°, 7.5°, 9.8°, 10.3°, 11.2°, 12.3°, 14.8°, 15.3°, 16.2°, 16.9°, 17.2°, 17.5°, 18.3°, 18.8°, 19.9°, 20.7°, 21.5°, 22.4°, 23.0°, 23.5°, and 25.8°±0.2 in 2θ. In yet another embodiment, Form A is characterized by an X-ray powder diffraction pattern substantially similar to FIG. 26.

In another embodiment, 1:1 Compound (I) fumarate Form A is characterized by differential scanning calorimeter (DSC) peak phase transition temperatures of 224±2° C.

Figure 29:
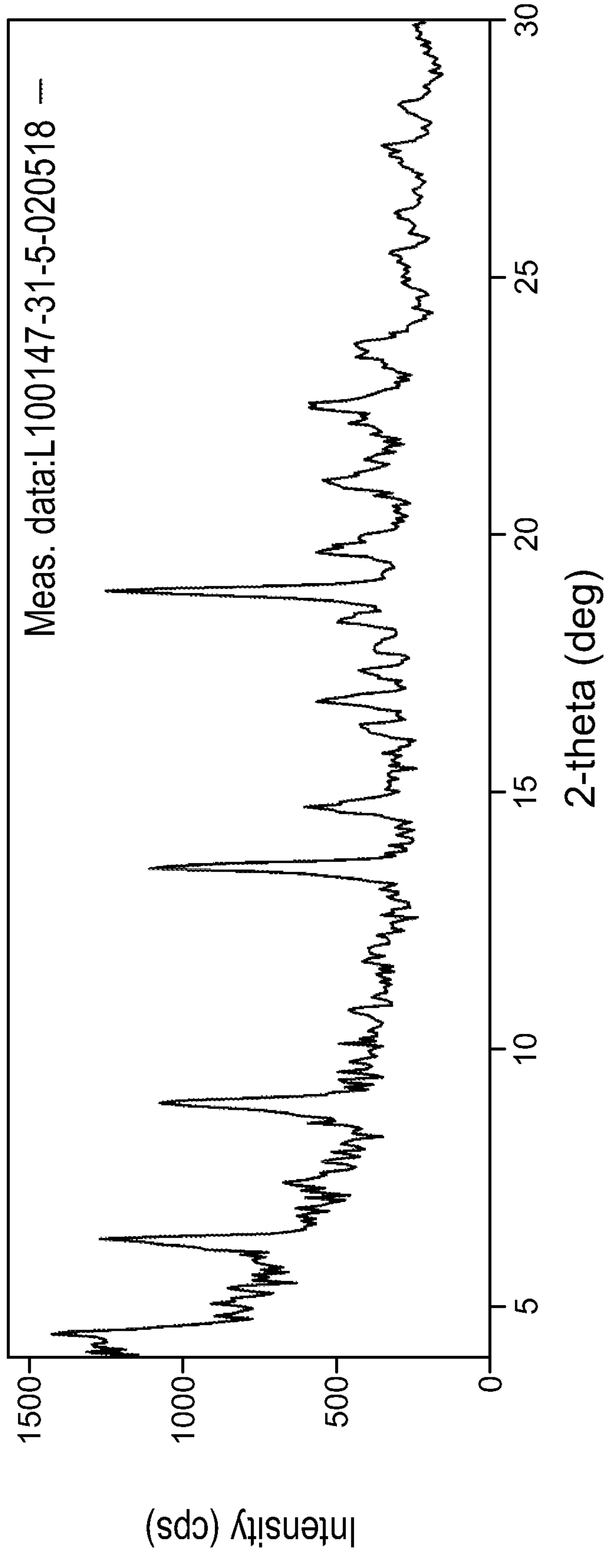
FIG. 29 shows the XRPD pattern of 1:1 Compound (I) crystalline Fumarate salt (Form C).

In one embodiment, 1:1 Compound (I) fumarate is a single crystalline form, Form C, characterized by an X-ray powder diffraction pattern which comprises at least three peaks (or four peaks) chosen from 6.3°, 9.0°, 13.5°, 18.9°, and 22.5°±0.2 in 2θ. In one embodiment, 1:1 Compound (I) fumarate is a single crystalline form, Form C, characterized by an X-ray powder diffraction pattern which comprises peaks at 6.3°, 9.0°, 13.5°, 18.9°, and 22.5°±0.2 in 2θ. In another embodiment, Form C is characterized by an X-ray powder diffraction pattern which comprises peaks at 4.5°, 6.3°, 9.0°, 13.5°, 14.7°, 18.9°, 19.7°, 21.0°, 22.5°, and 23.6°±0.2 in 2θ. In yet another embodiment, Form C is characterized by an X-ray powder diffraction pattern which comprises peaks at 4.5°, 6.3°, 7.4°, 9.0°, 13.5°, 14.7°, 16.2°, 16.8°, 17.4°, 17.8°, 18.4°, 18.9°, 19.7°, 21.0°, 22.5°, 23.6°, 25.5°, 26.2°, 27.5°, and 28.3°±0.2 in 2θ. In yet another embodiment, Form C is characterized by an X-ray powder diffraction pattern substantially similar to FIG. 29.

Figure 30:
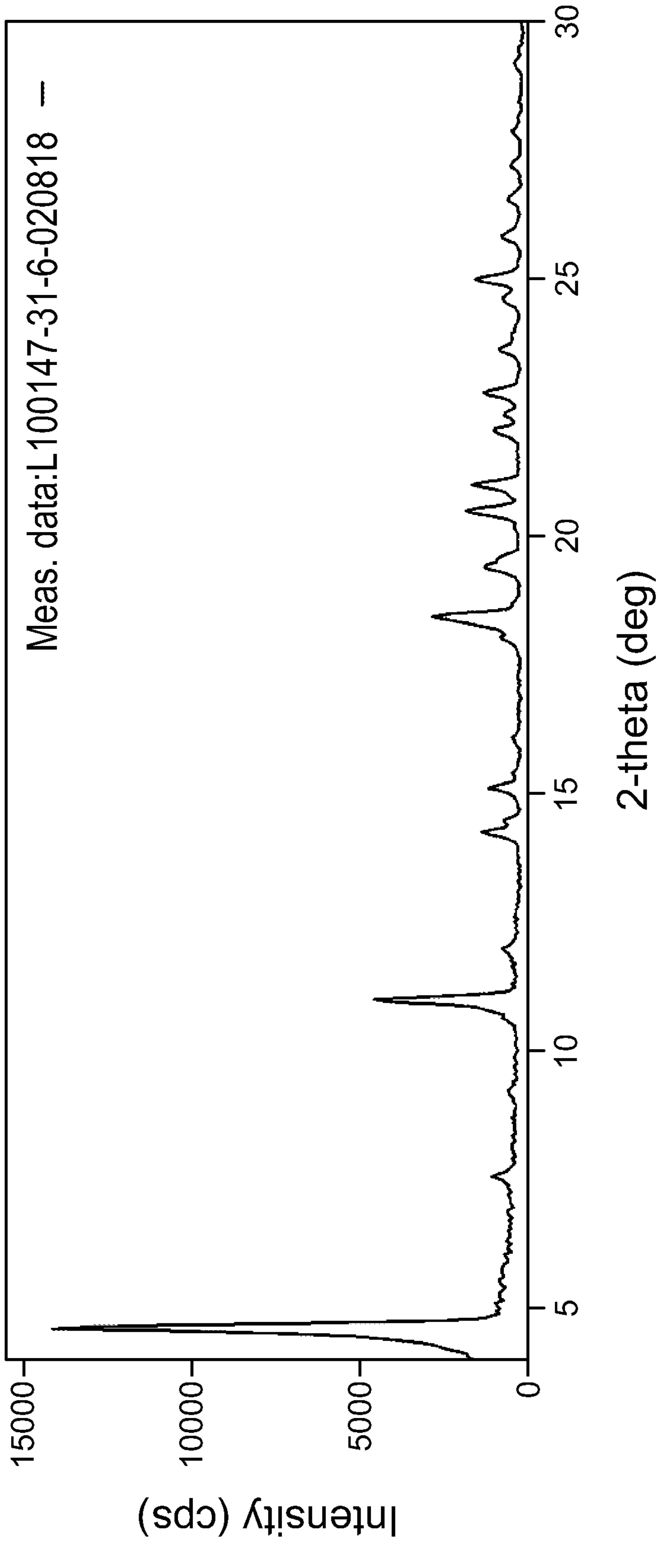
FIG. 30 shows the XRPD pattern of 1:1 Compound (I) crystalline Fumarate salt (Form D).

In one embodiment, 1:1 Compound (I) fumarate is a single crystalline form, Form D, characterized by an X-ray powder diffraction pattern which comprises at least three peaks (or four peaks) chosen from 4.6°, 11.0°, 18.5°, 20.5°, and 21.0°±0.2 in 2θ. In one embodiment, 1:1 Compound (I) fumarate is a single crystalline form, Form D, characterized by an X-ray powder diffraction pattern which comprises peaks at 4.6°, 11.0°, 18.5°, 20.5°, and 21.0°±0.2 in 2θ. In another embodiment, Form D is characterized by an X-ray powder diffraction pattern which comprises peaks at 4.6°, 11.0°, 15.1°, 18.5°, 19.4°, 20.5°, 21.0°, and 25.0°±0.2 in 2θ. In yet another embodiment, Form D is characterized by an X-ray powder diffraction pattern which comprises peaks at 4.6°, 11.0°, 12.0°, 14.3°, 15.1°, 18.5°, 19.4°, 20.5°, 21.0°, 22.8°, 23.6°, and 25.0°±0.2 in 2θ. In yet another embodiment, Form D is characterized by an X-ray powder diffraction pattern substantially similar to FIG. 30.

In one embodiment, 1:1 Compound (I) fumarate is a single crystalline form, Form C, in admixture with Form D, wherein Form C is characterized by an X-ray powder diffraction pattern which comprises at least three peaks (or four peaks) chosen from 6.3°, 9.0°, 13.5°, 18.9°, and 22.5°±0.2 in 2θ; and Form D is characterized by an X-ray powder diffraction pattern which comprises at least three peaks (or four peaks) chosen from 4.6°, 11.0°, 18.5°, 20.5°, and 21.0°±0.2 in 2θ.

In one embodiment, 1:1 Compound (I) fumarate is a single crystalline form, Form C, in admixture with Form D, wherein Form C is characterized by an X-ray powder diffraction pattern which comprises peaks at 6.3°, 9.0°, 13.5°, 18.9°, and 22.5°±0.2 in 2θ; and Form D is characterized by an X-ray powder diffraction pattern which comprises peaks at 4.6°, 11.0°, 18.5°, 20.5°, and 21.0°±0.2 in 2θ.

In one embodiment, 1:1 Compound (I) fumarate is a single crystalline form, Form C, in admixture with Form D, wherein Form C is characterized by an X-ray powder diffraction pattern which comprises peaks at 4.5°, 6.3°, 9.0°, 13.5°, 14.7°, 18.9°, 19.7°, 21.0°, 22.5°, and 23.6°±0.2 in 2θ; and Form D is characterized by an X-ray powder diffraction pattern which comprises peaks at 4.6°, 11.0°, 15.1°, 18.5°, 19.4°, 20.5°, 21.0°, and 25.0°±0.2 in 2θ.

In one embodiment, 1:1 Compound (I) fumarate is a single crystalline form, Form C, in admixture with Form D, wherein Form C is characterized by an X-ray powder diffraction pattern which comprises peaks at 4.5°, 6.3°, 7.4°, 9.0°, 13.5°, 14.7°, 16.2°, 16.8°, 17.4°, 17.8°, 18.4°, 18.9°, 19.7°, 21.0°, 22.5°, 23.6°, 25.5°, 26.2°, 27.5°, and 28.3°±0.2 in 2θ; and Form D is characterized by an X-ray powder diffraction pattern which comprises peaks at 4.6°, 11.0°, 12.0°, 14.3°, 15.1°, 18.5°, 19.4°, 20.5°, 21.0°, 22.8°, 23.6°, and 25.0°±0.2 in 2θ.

Pharmaceutical Compositions

Pharmaceutical compositions of the disclosure comprise a salt of Compound (I), or a crystalline form thereof described herein and one or more pharmaceutically acceptable carrier(s) or diluent(s). The term "pharmaceutically acceptable carrier" refers to a pharmaceutically acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the subject. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compositions of the disclosure may be administered orally, parenterally, by inhalation spray, topically, rectally, nasally, buccally, vaginally, or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In an embodiment, the compositions of the disclosure are administered orally, intraperitoneally or intravenously. Sterile injectable forms of the compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tween, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this disclosure may be orally administered in any orally acceptable dosage form including, but not limited to, capsules, tablets, aqueous suspensions, or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring, or coloring agents may also be added.

Alternatively, the pharmaceutically acceptable compositions of this disclosure may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this disclosure may also be administered topically, especially when the target of treatment includes areas or organs readily accessible by topical application, including diseases of the eye, the skin, or the lower intestinal tract. Suitable topical formulations are readily prepared for each of these areas or organs. Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

The pharmaceutically acceptable compositions of this disclosure may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of the compounds of the present disclosure that may be combined with the carrier to produce a composition in a single dosage form will vary depending upon the host treated, the particular mode of administration, and other factors determined by the person administering the single dosage form.

Dosages

Toxicity and therapeutic efficacy of a salt of Compound (I), or a crystalline form thereof described herein, can be determined by standard pharmaceutical procedures in cell cultures or experimental animals. The $LD_{50}$ is the dose lethal to 50% of the population. The $ED_{50}$ is the dose therapeutically effective in 50% of the population. The dose ratio between toxic and therapeutic effects ($LD_{50}/ED_{50}$) is the therapeutic index. A salt of Compound (I), or a crystalline form thereof that exhibits large therapeutic indexes are preferred. While a salt of Compound (I), or a crystalline form thereof described herein that exhibits toxic side effects may be used, care should be taken to design a delivery system that targets such salt or crystalline form to the site of affected tissue in order to minimize potential damage to uninfected cells and, thereby, reduce side effects.

Data obtained from the cell culture assays and animal studies can be used in formulating a range of dosage for use in humans. The dosage of such salts or crystalline forms may lie within a range of circulating concentrations that include the $ED_{50}$ with little or no toxicity. The dosage may vary within this range depending upon the dosage form employed and the route of administration utilized. For any salt of Compound (I), or a crystalline form thereof described herein, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

It should also be understood that a specific dosage and treatment regimen for any particular subject will depend upon a variety of factors, including but not limited to the activity of the specific compound employed, the age, body weight, general health, sex, diet, time of administration, rate of excretion, drug combination, and the judgment of the treating physician and the severity of the particular disease being treated. The amount of a salt of Compound (I), or a crystalline form of the present disclosure in the composition will also depend upon the particular compound in the composition.

Methods of Treatment

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

A "treatment" regime of a subject with an effective amount of the compound of the present disclosure may consist of a single administration, or alternatively comprise a series of applications. For example, 1:1 Compound (I) fumarate and 1:1 Compound (I) maleate may be administered at least once a week. However, in another embodiment, the compound may be administered to the subject from about one time per week to once daily for a given treatment. The length of the treatment period depends on a variety of factors, such as the severity of the disease, the age of the subject, the concentration and the activity of the compounds of the present disclosure, or a combination thereof. It will also be appreciated that the effective dosage of the compound used for the treatment or prophylaxis may increase or decrease over the course of a particular treatment or prophylaxis regime. Changes in dosage may result and become apparent by standard diagnostic assays known in the art. In some instances, chronic administration may be required.

Mutations in ALK2 cause the kinase to be inappropriately active and are associated with various diseases. Compound (I), its salt and crystal forms disclosed herein inhibit a mutant ALK2 gene, e.g., a mutant ALK2 gene that results in the expression of an ALK2 enzyme having an amino acid modification. In another aspect, Compound (I), its salt and crystal forms disclosed herein inhibit both wild type (WT) ALK2 protein and mutant forms of ALK2 protein. For the purposes of this disclosure, sequence information for ALK2 is found on the National Center for Biological Information (NCBI) webpage (https://www.ncbi.nlm.nih.gov/) under ACVR1 activin A receptor type 1 [*Homo sapiens* (human)]; Entrez Gene ID (NCBI): 90. It is also known as: FOP; ALK2; SKR1; TSRI; ACTRI; ACVR1A; ACVRLK2; said sequence information is incorporated herein.

In an embodiment, the disclosure provides a method of inhibiting aberrant ALK2 activity in a subject comprising the step of administering to the subject in need thereof a pharmaceutically effective amount of Compound (I), or the salt, crystal form or pharmaceutical composition described herein. In an embodiment, the aberrant ALK2 activity is caused by a mutation in an ALK2 gene that results in the expression of an ALK2 enzyme having an amino acid modification selected from one or more of L196P, PF197-8L, R202I, R206H, Q207E, R258S, R258G, R325A, G328A, G328V, G328W, G328E, G328R, G356D, and R375P. In an embodiment, the ALK2 enzyme has the amino acid modification R206H.

Because of their activity against ALK2, Compound (I), or the salt, crystal form or pharmaceutical composition described herein can be used to treat a subject with a condition associated with aberrant ALK2 activity. In an embodiment, the condition associated with aberrant ALK2 activity is fibrodysplasia ossificans progressiva. FOP diagnosis is based on the presence of congenital malformations of the great toes (hallux valgus) and the formation of fibrous nodules in soft tissues. The nodules may or may not transform into heterotopic bone. These soft tissue lesions are often first noted in the head, neck, or back. ~97% of FOP subjects have the same c.617G>A; R206H mutation in the ACVR1 (ALK2) gene. There is a genetic test available through the University of Pennsylvania (Kaplan et all, *Pediatrics* 2008, 121(5): e1295-e1300).

Other common congenital anomalies include malformations of the thumbs, short broad femoral necks, tibial osteochondromas and fused facet joints of the cervical spine. The fused facet joints in the neck often cause toddlers to scoot on their buttocks rather than crawl. FOP is commonly misdiagnosed (~80%; cancer or fibromatosis) and subjects are frequently subjected to inappropriate diagnostic procedures such as biopsies that exacerbate disease and cause permanent disability.

In an embodiment, the present disclosure provides a method of treating or ameliorating fibrodysplasia ossificans progressiva in a subject, comprising administering to the subject in need thereof a pharmaceutically effective amount of Compound (I), or the salt, crystal form or pharmaceutical composition described herein.

In an embodiment, the condition associated with aberrant ALK2 activity is fibrodysplasia ossificans progressiva (FOP) and the subject has a mutation in an ALK2 gene that results in the expression of an ALK2 enzyme having an amino acid modification selected from one or more of L196P, PF197-8L, R202I, R206H, Q207E, R258S, R258G, R325A, G328A, G328W, G328E, G328R, G356D, and R375P. In one aspect of this embodiment, the ALK2 enzyme has the amino acid modification R206H.

The present disclosure includes methods of identifying and/or diagnosing subjects for treatment with Compound (I), or the salt, crystal form or pharmaceutical composition described herein. In an embodiment, the disclosure provides a method of detecting a condition associated with aberrant ALK2 activity e.g., FOB in a subject, wherein the method includes a. obtaining a sample e.g., plasma from the subject e.g., a human subject; and b. detecting whether one or more mutations in an ALK2 gene as described herein are present in the sample. In another embodiment, the disclosure provides a method of diagnosing a condition associated with aberrant ALK2 activity in a subject, said method comprising: a. obtaining a sample from the subject; b. detecting whether one or more mutations in an ALK2 gene as described herein are present in the sample using a detection method described herein; and c. diagnosing the subject with the condition when the presence of the one or more mutations is detected. Methods for detecting a mutation include but are not limited to hybridization-based methods, amplification-based methods, microarray analysis, flow cytometry analysis, DNA sequencing, next-generation sequencing (NGS), primer extension, PCR, in situ hybridization, dot blot, and Southern blot. In an embodiment, the present disclosure provides a method of diagnosing and treating a condition associated with aberrant ALK2 activity in a subject, said method comprising a. obtaining a sample from a subject; b. detecting whether one or more mutations in an ALK2 gene as described herein are present in the sample; diagnosing the subject with the condition when the one or more mutations in the sample are detected; and administering an effective amount of Compound (I), or the salt, crystal form or pharmaceutical composition described herein to the diagnosed subject. In an embodiment, the disclosure provides a method of treating a condition associated with aberrant ALK2 activity in a subject, said method comprising a. determining if, having determined if, or receiving information that the subject has one or more mutations in an ALK2 gene as described herein; b. identifying the subject as responsive to one or more compounds or a pharmaceutical composition described herein; and c. administering an effective amount of Compound (I), or the salt, crystal form or pharmaceutical composition to the subject.

In an embodiment, the condition associated with aberrant ALK2 activity is a brain tumor, e.g., glial tumor. In an embodiment, the glial tumor is diffuse intrinsic pontine glioma (DIPG). In an embodiment, the disclosure provides a method of treating or ameliorating diffuse intrinsic pontine glioma in a subject, comprising administering to the subject in need thereof a pharmaceutically effective amount of Compound (I), or the salt, crystal form or pharmaceutical composition described herein.

In an embodiment, the condition associated with aberrant ALK2 activity is diffuse intrinsic pontine glioma and the subject has a mutation in an ALK2 gene that results in the expression of an ALK2 enzyme having an amino acid modification selected from one or more of R206H, G328V, G328W, G328E, and G356D. In one aspect of this embodiment, the ALK2 enzyme has the amino acid modification R206H.

In an embodiment, the condition associated with aberrant ALK2 activity is anemia associated with inflammation, cancer or chronic disease.

In an embodiment, the condition associated with aberrant ALK2 activity is trauma- or surgery-induced heterotopic ossification.

In an embodiment, a compound of the disclosure is co-administered (either as part of a combination dosage form or as a separate dosage form administered prior to, sequentially with, of after administration) with a second therapeutic agent useful in treating the disease to be treated e.g., FOP. In one aspect of this embodiment, a compound of the disclosure is co-administered with a steroid (e.g., prednisone) or other anti-allergenic agents such as omalizumab.

In an embodiment, a compound of the disclosure is co-administered with a RAR-γ agonist or an antibody against activin for treating the disease to be treated e.g., FOP. In an embodiment, the RAR-γ agonist to be co-administered is palovarotene. In an embodiment, the antibody against activin to be co-administered is REGN2477.

In an embodiment, a compound of the disclosure is co-administered with therapies that target mast cells useful in treating FOP. In an embodiment, a compound of the disclosure is co-administered with a mast cell inhibitor including, but not limited to a KIT inhibitor. In an embodiment, the mast cell inhibitor to be co-administered is selected from cromolyn sodium (or sodium cromoglicate); brentuximab (ADCETRIS®); ibrutinib) (IMBRUVICA®); omalizumab (XOLAIR®); anti-leukotriene agents (e.g., montelukast (SINGULAIR®) or zileuton (ZYFLO® or ZYFLO CR®); and KIT inhibitors (e.g., imatinib (GLEEVEC®), midostaurin (PKC412A), masitinib (MASIVET® or KINAVET®), avapritinib, DCC-2618, PLX9486).

The following examples are intended to be illustrative and are not intended to be limiting in any way to the scope of the disclosure.

EXPERIMENTAL

Abbreviations:

| Abbreviation | Solvent |
|---|---|
| ACN | Acetonitrile |
| DCM | Dichloromethane |
| DMAc | N,N-Dimethylacetamide |
| DMF | N,N-Dimethylformamide |
| EtOAc | Ethyl Acetate |
| IPA | 2-Propanol |
| MBK | Methyl Butyl Ketone |
| MEK | Methyl Ethyl Ketone |
| MeOH | Methanol |
| MtBE | tert-Butyl Methyl Ether |
| 1-PA | 1-Propanol |
| TFE | Trifluoroethanol |
| BA | Benzyl Alcohol |
| DEE | Diethyl ether |
| DMSO | Dimethylsulfoxide |
| EtOH | Ethanol |
| IPOAc/IPAc | Isopropyl acetate |
| MCH | Methylcyclohexane |
| MeOAc | Methyl Acetate |
| MIBK | 4-Methyl-2-pentanone |
| NMP | N-Methyl Pyrrolidone |
| TFA | Trifluoroacetic Acid |
| THF | Tetrahydrofuran |

| Instruments | |
|---|---|
| Full Name | Abbreviation |
| Differential scanning calorimetry | DSC |
| Dynamic Vapor Sorption | DVS |
| High Performance Liquid Chromatography | HPLC |
| Karl Fischer Titration | KF |
| Nuclear Magnetic Resonance | NMR |
| X-ray Powder Diffraction | XRPD |
| Thermogravimetric Analysis | TGA |

| Units | |
|---|---|
| Full Name | Abbreviation |
| Celsius | C. |
| Degrees | ° |
| Equivalents | eq. |
| Gram | g |
| Hour | h |
| Kelvin | K |
| Liters | L |
| Milligrams | mg |
| Milliliters | mL |
| Minute | min |
| Milliamp | mA |
| Kilovolt | kV |
| Relative Humidity | RH |
| Room temperature | RT |
| Second | sec |
| volume | vol. |
| Volume ratio | v/v |
| Watt | W |
| Weight | wt. |
| Weight Percentage | wt. % |

Analysis Conditions

X-Ray Powder Diffraction (XRPD)

Powder X-ray diffraction was done using a Rigaku Mini-Flex 600 or a Bruker D8 Advance equipped with Lynxeye detector in reflection mode (i.e. Bragg-Brentano geometry). Samples were prepared on Si zero-return wafers. A typical scan is from 2θ of 4 to 30 degrees, with step size 0.05 degrees over five minutes with 40 kV and 15 mA. A high-resolution scan is from 2θ of 4 to 40 degrees, with step size 0.05 degrees over thirty minutes with 40 kV and 15 mA. Typical parameters for XRPD are listed below.

| Parameters for Reflection Mode | |
|---|---|
| X-ray wavelength | Cu Kα1, 1.540598 Å, |
| X-ray tube setting | 40 kV, 40 mA (or 15 mA) |
| Slit condition | Variable + Fixed Slit System (0.6 mm div. + 2.5° soller) |
| Scan mode | Step or Continuous |
| Scan range (°2θ) | 4-30 |
| Step size (°2θ) | 0.02 or 0.05 |
| Dwell time (s/step) | 0.15 |
| Scan speed (°/min) | 5 |
| Spin | Yes (0.5 Hz) |

Thermogravimetric Analysis and Differential Scanning Calorimetry (TGA & DSC)

Thermogravimetric analysis and differential scanning calorimetry was done on the same sample simultaneously using a Mettler Toledo TGA/DSC$^{3+}$. The desired amount of sample is weighed directly in a hermetic aluminum pan with pin-hole. A typical sample mass for the measurement is 5-10 mg. A typical temperature range is 30° C. to 300° C. at a heating rate of 10° C. per minute (total time of 27 minutes). Protective and purge gasses are nitrogen (20-30 mL/min and 50-100 mL/min). Typical parameters for DSC/TGA are listed below.

| Parameters | |
|---|---|
| Method | Ramp |
| Sample size | 5-10 mg |
| Heating rate | 10.0° C./min |
| Temperature range | 30 to 300° C. |

Differential Scanning Calorimetry (DSC)

1-5 mg of material was weighted into an aluminum DSC pan and sealed non-hermetically with an aluminum lid. The sample pan was then loaded into a TA Instruments Q2000 (equipped with a cooler). Once a stable heat-flow response was obtained at 30° C., the sample and reference were heated to 300° C. at a rate of 10° C./min and the resulting heat flow response was monitored. Prior to analysis, the instrument was temperature and heat-flow calibrated using an indium reference standard. Sample analysis was carried out with the help of TA Universal Analysis 2000 software where the temperatures of thermal events were quoted as the onset and peak temperature, measured according to the manufacturer's specifications. Method gas: $N_2$ at 60.00 mL/min.

$^1$H-Nuclear Magnetic Resonance Spectroscopy ($^1$H-NMR)

Proton NMR was done on a Bruker Avance 300 MHz spectrometer. Solids were dissolved in 0.75 mL deuterated solvent in a 4 mL vial and transferred to an NMR tube (Wilmad 5 mm thin wall 8" 200 MHz, 506-PP-8). A typical measurement is usually 16 scans. Typical parameters for NMR are listed below.

| Parameters - Bruker Avance 300 | |
|---|---|
| Instrument | Bruker Avance 300 MHz spectrometer |
| Temperature | 300 K |
| Probe | 5 mm PABBO BB-1H/DZ-GRD Z104275/0170 |
| Number of scans | 16 |
| Relaxation delay | 1.000 s |
| Pulse width | 14.2500 μs |
| Acquisition time | 2.9999 s |
| Spectrometer frequency | 300.15 Hz |
| Nucleus | 1H |

Dynamic Vapor Sorption (DVS)

Dynamic Vapor Sorption (DVS) was done using a DVS Intrinsic 1. The sample was loaded into a sample pan and suspended from a microbalance. A typical sample mass for DVS measurement is 25 mg. Nitrogen gas bubbled through distilled water provides the desired relative humidity. The sample was held for a minimum of 5 min at each level and only progressed to the next humidity level if there was <0.002% change in weight between measurements (interval: 60 seconds) or 240 min had elapsed. A typical measurement comprises the steps:

1—Equilibrate at 50% RH

2—50% to 2%. (50%, 40%, 30%, 20%, 10% and 2%)

a. Hold minimum of 5 mins and maximum of 60 minutes at each humidity. The pass criteria is less than 0.002% change 3—2% to 95% (2%, 10%, 20%, 30%, 40%, 50%, 60%, 70%, 80%, 90%, 95%)

a. Hold minimum of 5 mins and maximum of 60 minutes at each humidity. The pass criteria is less than 0.002% change 4—95% to 2% (95%, 80%, 70%, 60%, 50%, 40%, 30%, 20%, 10%, 2%)
   a. Hold minimum of 5 mins and maximum of 60 minutes at each humidity. The pass criteria is less than 0.002% change 5—2% to 50% (2%, 10%, 20%, 30%, 40%, 50%)
   a. Hold minimum of 5 mins and maximum of 60 minutes at each humidity. The pass criteria is less than 0.002% change High Performance Liquid Chromatography (HPLC)

Agilent 1220 Infinity LC: High performance liquid chromatography (HPLC) was conducted using an Agilent 1220 Infinity LC. Flow rate range is 0.2-5.0 mL/min, operating pressure range is 0-600 bar, temperature range is 5° C. above ambient to 60° C., and wavelength range is 190-600 nm.

| Parameters | | | |
|---|---|---|---|
| Mobile Phase A | 0.05% TFA in distilled water | | |
| Mobile Phase B | 0.05% TFA in ACN | | |
| Diluent | ACN:water (25:75 vol) | | |
| Injection Volume | 5 μL | | |
| Monitoring Wavelength | 256 nm | | |
| Column | Supelco Ascentis Express, C18, 4.6 × 150 mm, 2.7 μm | | |
| Column Temperature | 30° C. | | |
| Gradient Method | Time (min) | % A | Flow rate (mL/min) |
| | 0 | 90 | 1.50 |
| | 4 | 80 | 1.50 |
| | 15 | 70 | 1.50 |
| | 20 | 5 | 1.50 |
| | 23 | 5 | 1.50 |
| | 23.1 | 90 | 1.50 |
| | 28 | 90 | 1.50 |

Karl Fischer Titration

Karl Fischer titration for water determination was done using a Mettler Toledo C20S Coulometric KF Titrator equipped with a current generator cell with a diaphragm, and a double-platinum-pin electrode. Aquastar™ CombiCoulomat fritless reagent was used in both the anode and cathode compartments. Samples of approximately 0.03-0.10 g were dissolved in the anode compartment and titrated until the solution potential dropped below 100 mV. Hydranal 1 wt. % water standard is used for validation prior to sample analysis.

Microscopy

Optical microscopy was performed using a Zeiss Axio-Scope A1 equipped with 2.5×, 10×, 20× and 40× objectives and polarizer. Images are captured through a built-in Axiocam 105 digital camera and processed using ZEN 2 (blue edition) software provided by Zeiss.

Example 1: Combinatorial Salt Screening

1.1 Salt Screening

The free base of Compound (I) has multiple pKa's according to Marvin Sketch software predictions. The compound has three basic nitrogen with theoretical pKa values of 8.95, 3.57, and 2.86. Theoretical log P is 2.98.

Salt screening was carried out using 13 different counter-ions. All counter-ions were tested with 1.1 equivalents. HCl was also tested using 2.2 equivalents of counter-ion and sulfuric acid was tested using 0.5 equivalents of counter-ion. A list of the counter-ions is provided in Table 1.

A stock solution of Compound (I) was prepared in anhydrous EtOH (20 wt. %, density 0.8547 g/mL). Stock solutions of all counter-ions were also prepared in EtOH. Counter-ion stock solutions of solid counter-ions were prepared to be 0.02 g/mL and liquid counter-ions were prepared to be 10% by volume.

Salt formation was carried out at room temperature in 2 mL vials. 25 mg of Compound (I) (145.6 μL stock solution) and 1.1 equivalents of counter-ion were added to each vial. In the case of sulfuric acid, 0.55 and 1.1 equivalents counter-ion was added. In the case of HCl, 1.1 and 2.2 equivalents counter-ion was added. Solvent was allowed to evaporate at 30° C. while stirring overnight and then put at 50° C. under vacuum to thoroughly dry for 4 hours.

Approximately 25 volumes solvent (0.625 mL) were added to each vial for screening. The three solvents selected were EtOH, EtOAc, and IPA:water (9:1 vol). Once solvents were added, the mixtures (or solutions) were heated to 45° C., held for 1.5 hours, cooled to room temperature and stirred overnight. When slurries were formed, solids were filtered for XRPD analysis.

XRPD analysis was done in three stages. XRPD of the wet cake was done for all samples (where solids were observed). Unique solids were then left on XRPD plates and dried under vacuum at 50° C. for at least 3 hours. XRPD of unique dry solids was then done. Solids were then exposed to >90% relative humidity for one day and XRPD on resulted solids was done. The humid environment was generated by placing a beaker of saturated potassium sulfate in water in a sealed container. All XRPD patterns were compared to counter ion XRPD patterns and known free molecule patterns.

If solids were not formed with the first three screening solvents (EtOH, EtOAc, IPA:water) the caps were opened and solvent was allowed to evaporate at 30° C. while stirring. Solids were evaporated to dryness by placing under vacuum at 50° C. for 3-4 hours and a second round of solvents was added (IPOAc, MBK, MtBE). If solids were not formed with the second round of solvents, solvent was again evaporated to dryness and DEE was added.

TABLE 1

Counter ions used in initial salt screening and associated pKa values.

| ID | Counter Ion | pKa (lowest) | Equivalents used for screening |
|---|---|---|---|
| 1 | Acetic Acid | 4.75 | 1.1 |
| 2 | Benzenesulfonic Acid | −2.8 | 1.1 |
| 3 | Benzoic Acid | 4.19 | 1.1 |
| 4 | Citric Acid | 3.08 | 1.1 |
| 5 | Fumaric Acid | 3.03 | 1.1 |
| 6 | Hydrochloric Acid | −7 | 1.1, 2.2 |
| 7 | Malic Acid | 3.4 | 1.1 |
| 8 | Maleic Acid | 1.9 | 1.1 |
| 9 | Phosphoric Acid | 2.15 | 1.1 |
| 10 | Salicylic Acid | 2.97 | 1.1 |
| 11 | Sulfuric Acid | −3 | 0.55, 1.1 |
| 12 | Succinic Acid | 4.2 | 1.1 |
| 13 | Tartaric Acid | 2.89 | 1.1 |

Crystalline solids were observed when screening with benzenesulfonic acid (BSA), benzoic acid, fumaric acid, HCl (1 and 2 equivalents), maleic acid, salicylic acid, and succinic acid. One unique XRPD pattern was observed with BSA, benzoic acid, HCl (2 eq.), salicylic acid, and succinic acid. Multiple patterns were observed with HCl (1 eq) and fumaric acid. Two patterns were observed with maleic acid and both deliquesced on humidity exposure. Of the crystal line solids, the solids resulting from screening with benzoic acid, fumaric acid, HCl (1 eq.), salicylic acid, and succinic acid did not deliquesce upon humidity exposure.

Crystalline salts were characterized and evaluated for viability based on melting point, crystallinity, stability on drying and humidity exposure, water solubility, polymorphism, and acceptability of counter-ion.

The fumarate exhibited high solubility in water and simulated fluids (>15 m/mL in all fluids), and a hypothesized hydrate, designated Form B, was stable on drying and humidity exposure. Form A (anhydrous) exhibited high melting (onset 221° C.).

A summary of the physicochemical properties of the freebase and select salts is given in Table 2 below.

TABLE 2

Physicochemical properties of the freebase and select salts

| Salt | DSC Onset(s) ° C. | TGA Mass Loss (wt. %) | DVS Mass Change (wt. %) | Stoichiometry | Solubility at 37° C. (mg/mL) Water | FaSSIF | FaSSGF |
|---|---|---|---|---|---|---|---|
| Freebase | 116.2 | 0.22 | 0.88-0.92 | n/a | 0.08 | 17.9 | 7.29 |
| Mono-HCl Form A | 47.4, (dehydration)203.0 | 2.82, 0.44 | 1.30-1.43 | mono- | 33.4 | 30.9 | 6.96 |
| Succinate Form A | 172.9 | 0.27 | 0.59-0.60 | sesqui- | >34.0 | >22.2 | >25.9 |
| Fumarate Form A | 221.4 | 1.27 (up to 220° C.) | | mono- | | | |

Mono-HCl salt, succinate, and fumarate were selected for further development in view of acceptable physicochemical properties. The freebase was also included in further characterization for comparison.

Benzoate was not selected due to poor water solubility and high mass loss on melting. Salicylate was not selected due to poor water solubility, high mass loss on melting, and possibly being polymorphic. Besylate, maleate, and bis-HCl were not selected due to low crystallinity and instability in a humid environment (deliquesced).

The free base sample showed melting onset at 116.19° C. in DSC. The TGA thermogram showed a gradual mass loss of 0.16 wt. % prior to melting and a step mass loss of 0.05 wt. % on melting. The solid was fines by microscopy. Karl Fischer titration of freebase showed 0.37 wt. % water.

The freebase exhibited high solubility in many organic solvent systems (>200 mg/mL at room temperature in most organic solvents tested), high solubility in simulated fluids (0.08 mg/mL water, ~17 mg/mL fasted state simulated gastric fluid, ~7 mg/mL fasted state simulated intestinal fluid), an acceptable melting (onset 116° C.), and low residual solvent (<0.20 wt. % by thermogravimetric analysis). Disadvantages to the freebase are that it was polymorphic (4 patterns observed during limited screening) and was physically unstable in humid environment (>90% relative humidity) and turned into a sticky gum within 4 days, and it gums in water. Lab-scale results also indicated that the free base would be difficult to isolate as crystalline solid on manufacture scale.

The mono-HCl salt exhibited high melting (onset 203° C.), is a hydrate (channel hydrate), and has high crystallinity by X-ray powder diffraction. It has high solubility in water and simulated fluids (>30 mg/mL water and fasted state simulated gastric fluid, ~7 mg/mL fasted state simulated intestinal fluid). Disadvantages to the mono-HCl salt include sensitivity to equivalents added (bis-HCl salt formed with as low as 1.3 molar equivalents HCl), and sensitivity to drying.

The succinate showed only one pattern during screening, was stable on drying and humidity exposure, was less hygroscopic than the mono-HCl salt and freebase, exhibited high solubility in water and simulated fluids (>22 m/mL in all fluids), high melting (onset 173° C.), and acceptable mass loss by thermogravimetric analysis on melting (0.27 wt. %).

1.2 Humidity Exposure of the Free Base

A crystalline form of the free base was exposed to high humidity (>90% RH) overnight. The humid environment was generated by placing a beaker of saturated potassium sulfate in water in a sealed container.

The solids remained as the same crystalline form after overnight humidity exposure, but lost some crystallinity. The same sample was placed back in the humid environment after XRPD analysis. After one week, it was noted that the sample had deliquesced on the XRPD plate. A second experiment was started in the same conditions. The solid became darker in color and sticky. XRPD of the sample was taken at 6 days. The intensity of the peaks was lower and a change in baseline was observed which is indicative of increased amorphous content.

Example 2: Preparations and Characterization of Crystalline Form of 1.5:1 Compound (I) Sesqui-Succinate (Form A)

2.1 Preparations

Method A:

Compound (I) in freebase was weighed in a 4 mL vial and adding 1.1 equivalents of succinic acid. EtOH (15 volumes) was then added at room temperature. Solids dissolved and remained in solution. The slurry was heated to 45° C. and held for two hours while stirring followed by cooling naturally to room temperature. Solids still remained in solution, so the solution was seeded with sample succinate obtained from screening. Seed was retained and a white slurry formed quickly. The slurry was stirred at room temperature overnight. Prior to filtration the slurry was a medium thickness beige/off-white slurry. The slurry was filtered and washed twice with 2 volumes EtOH then dried at 50° C. under vacuum overnight. Purity by HPLC was 99.79 area %. The solid obtained was further characterized by XRPD (see FIG. 1 and Table 3), TGA-DSC (FIG. 2), $^{1}$H NMR (FIG. 3), and single crystal X-ray crystallography.

Figure 2:
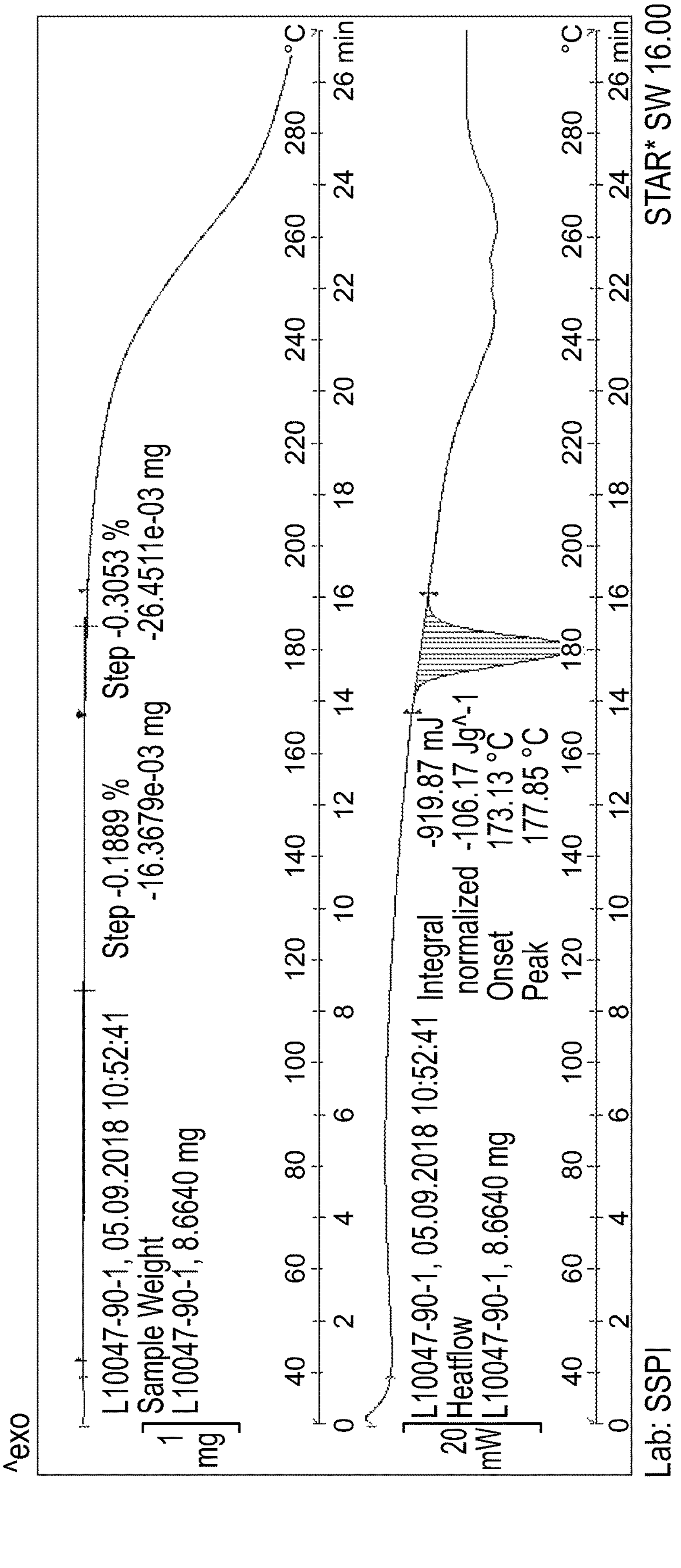
FIG. 2 shows the Thermogravimetric Analysis (TGA) and Differential Scanning calorimetry Analysis (DSC) thermograms of 1.5:1 Compound (I) Sesqui-Succinate.
Figure 3:
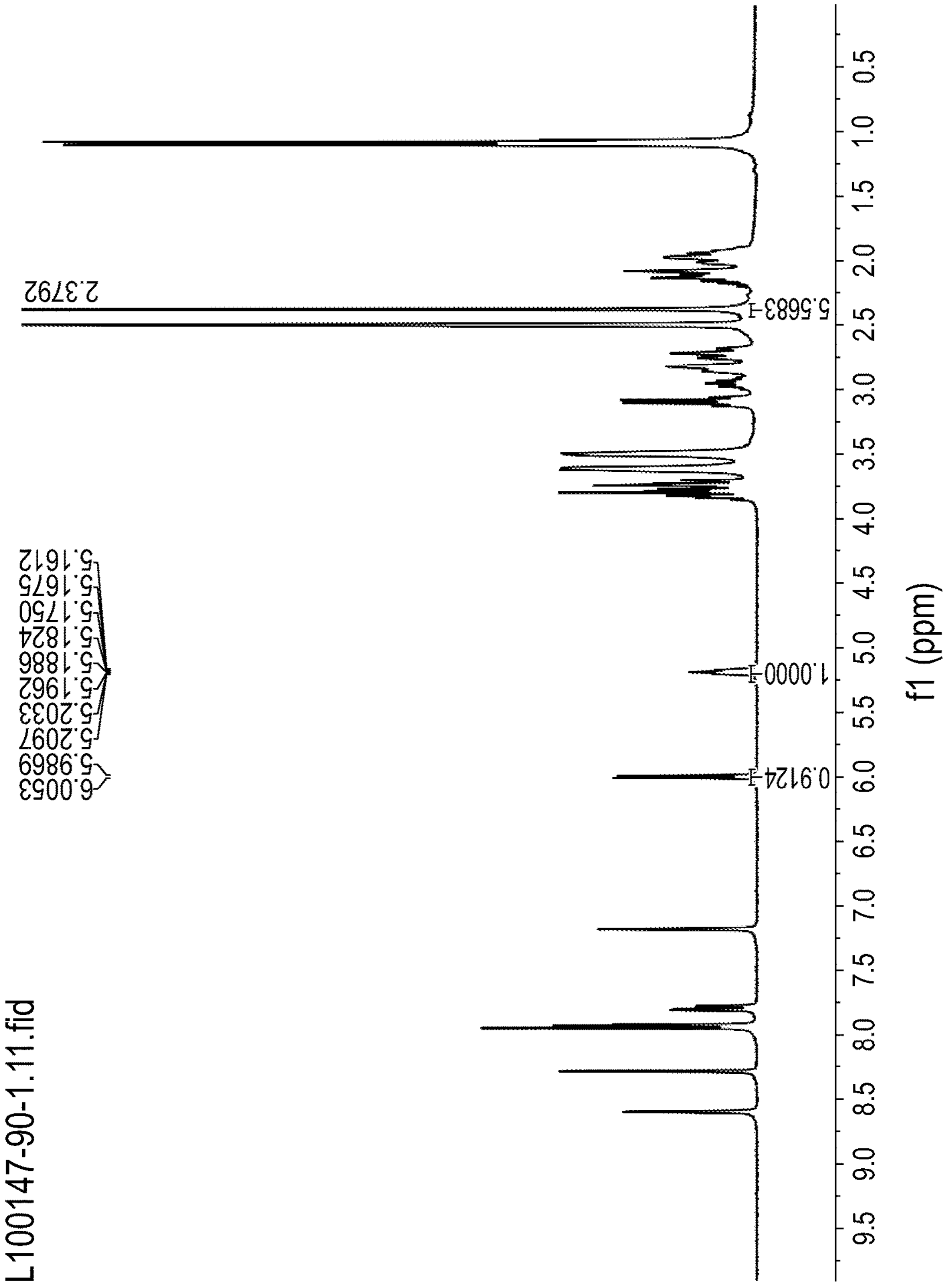
FIG. 3 shows the $^1$H-Nuclear Magnetic Resonance Spectroscopy ($^1$H-NMR) of 1.5:1 Compound (I) Sesqui-Succinate.

Initial mass loss by TGA was 0.19 wt. % followed by 0.30 wt. % upon melting, see FIG. 2. The DSC thermogram showed melting with an onset of 172.9° C., followed by decomposition of the sample above 200° C.

TABLE 3

XRPD of Compound (I) Sesqui-Succinate (Form A)

| 2θ (deg) | d-Spacing (ang.) | Relative Intensity (%) |
|---|---|---|
| 4.28 | 20.61 | 25 |
| 6.71 | 13.16 | 10 |
| 8.50 | 10.39 | 42 |
| 12.76 | 6.93 | 20 |
| 14.04 | 6.30 | 25 |
| 15.42 | 5.74 | 57 |
| 15.66 | 5.65 | 10 |
| 16.61 | 5.33 | 8 |
| 17.00 | 5.21 | 22 |
| 18.13 | 4.89 | 8 |
| 19.43 | 4.56 | 8 |
| 19.76 | 4.49 | 13 |
| 20.12 | 4.41 | 17 |
| 20.74 | 4.28 | 11 |
| 21.29 | 4.17 | 100 |
| 22.36 | 3.97 | 6 |
| 24.98 | 3.56 | 7 |
| 29.10 | 3.07 | 7 |
| 34.35 | 2.61 | 7 |

Method B:

Salt formation was carried out using several different solvent conditions using Compound (I) freebase and 1.6 equivalents succinic acid. About 30 mg freebase was weighed into a 2 mL vial and 10 volumes solvent were added. In all solvents except, MtBE, the freebase dissolved at room temperature. Succinic acid was then added as a stock solution in EtOH, bringing each solvent composition to about 40% EtOH by volume. Solutions/slurries were stirred at room temperature until precipitation was observed and then solids were collected for XRPD analysis. A summary of the solids obtained from salt formation experiments is given in Table 4.

TABLE 4

Summary of solids obtained from salt formation experiments.

| Solvent | XRPD Pattern | Observations |
|---|---|---|
| acetone:EtOH (62:38 vol) | Form A | dissolved then formed thick slurry after ~5 h |
| EtOH | Form A | dissolved then formed slurry within 5 min |
| IPA:EtOH (62:38 vol) | Form A | dissolved then formed slurry within 5 min, slightly gummy |
| EtOAc:EtOH (62:38 vol) | Form A | dissolved then formed slurry within 5 min, off-white powder |
| 1,4-dioxane:EtOH (62:38 vol) | Form A | peach solution then formed a slurry after 1 day |
| ACN:EtOH (62:38 vol) | Form A | dissolved then formed thick white slurry in ~1.5 h |
| toluene:EtOH (62:38 vol) | Form A | dissolved then formed flowable off-white slurry in ~1.5 h |
| MtBE:EtOH (62:38 vol) | Form A | dissolved when SA added, formed slurry within 5 min |

Method C: Amorphous Slurries

About 30 mg of Compound (I) Sesqui-Succinate was melted in 2 mL vials to produce amorphous glass-like solid. Solvent (450 μL) was added to each vial along with a stir bar at room temperature. In all cases, the glass-like solid was stuck to the bottom of the vial so a spatula was used to loosen the solid and ensure proper mixing. In many instances, a light brown slurry was formed immediately after loosening solids. Slurries were sampled for XRPD analysis as precipitation was observed. The earliest time point for sampling was approximately 30 minutes after solvent addition. The results and observations from the amorphous slurry experiments are summarized in Table 5.

TABLE 5

Summary of XRPD patterns of solids obtained from amorphous slurry experiments.

| Solvent | Sampling Time (h) | XRPD Pattern | Observations |
|---|---|---|---|
| acetone | 0.5 | Form A | light brown slurry/beige solid |
| EtOH | 0.5 | Form A | light brown slurry/beige solid |
| IPA | 0.5 | Form A | light brown slurry/beige solid |
| EtOAc | 4.25 | Form A | initially brown gum then off white slurry + brown gum |
| IPOAc | 0.5 | Form A | off white slurry + brown gum/light solid |
| 1,4-dioxane | 0.5 | Form A | light brown solution then precipitated to light brown slurry |
| toluene | | solution | brown gum |
| MtBE | 0.5 | Form A (low crystallinity) | light brown slurry + brown gum |
| MIBK | 4.25 | Form A | light brown solution then off-white slurry + white film on vial |
| ACN | 0.5 | Form A | light brown slurry |

Method D: Amorphous Vapor Diffusion

About 10 mg of amorphous Compound (I) Sesqui-Succinate was placed in 4 mL vials. Each 4 mL vial was then placed in a 20 mL vial containing 3 mL solvent and sealed. The vials were held at room temperature over a weekend prior to sampling solids for XRPD. Most solids changed in appearance from a light beige glass (broken up from amorphous foam) to a white/off-white powder. The amorphous solid exposed to humid atmosphere (water as solvent) became a yellow paste. A summary of the solids obtained from amorphous vapor diffusion experiments is outlined in Table 6.

TABLE 6

Summary of solids obtained from amorphous vapor diffusion experiments.

| Solvent | XRPD Pattern | Observations |
|---|---|---|
| EtOH | Form A | white/off-white powder |
| acetone | Form A | white/off-white powder |
| EtOAc | Form A | white/off-white powder, somewhat stuck to bottom of vial |
| 1,4-dioxane | Form A | white/off-white powder- wet texture |
| toluene | Form A | white/off-white powder- stuck to bottom of vial |
| DMSO | Form A | white/off-white powder- wet texture |
| MIBK | Form A | white/off-white chunks- stuck to vial |
| water | Form A | yellow paste (wet) |

In the polymorph screening on Compound (I) Sesqui-Succinate, solids were generated using more than 10 crystallization or salt formation methods, including experiments utilizing amorphous solid. Only crystalline Form A and an amorphous solid were observed throughout the polymorph screening of Compound (I) Sesqui-Succinate.

A sample of amorphous solid (Compound (I) Sesqui-Succinate) was heated to 140° C. followed by cooling to room temperature. Resulting solids were crystalline Form A by XRPD.

Amorphous solid (Compound (I) Sesqui-Succinate) was exposed to 75% RH/40° C. for one week. Solids changed in appearance from a light beige yellow solid to a hard, yellow glass. XRPD of the solids showed crystalline Form A.

Form A was found to be crystalline with a melting onset of 173° C., was stable on drying and humidity exposure, and exhibited high solubility in water and simulated fluids (>22 mg/mL in all fluids.

Method E:

Intermediate 6-(5-(4-ethoxy-1-isopropylpiperidin-4-yl)pyridin-2-yl)-4-(piperazin-1-yl)pyrrolo[1,2-b]pyridazine (3.5 kg, 7.8 mol), which was disclosed in U.S. Pat. No. 10,233,186, was dissolved in isopropyl acetate (IPAc, 2.75 volumes) containing (R)-tetrahydrofuran-3-yl 1H-imidazole-1-carboxylate (1.2 equiv). The mixture was heated and agitated until complete conversion. Additional IPAc (4 volumes) was added as the reaction is quenched with aqueous ammonia (2 vol). Phase separations, water washes, and a distillation give a dry IPAc solution of Compound (I) (~3.5 kg in 3 volumes). While heating at 40-60° C., succinic acid in ethanol (1.45 equiv in 10 volumes) was added. The mixture is heated to 75-85° C. for 30 minutes. After cooling to 70-75° C., the solution was seeded with Compound (I) Sesqui-Succinate and cooled to 10° C. over 8 hours. The suspension was isolated by filtration and washed with ethanol (2×3 volumes) to give Compound (I) Sesqui-Succinate Form A.

2.2 Humidity Exposure

The Sesqui-Succinate obtained in Example 2.1 was exposed to 75% relative humidity at 40° C. for one week. The samples were placed in a 4 mL vial covered with a Kimwipe® and then placed in a 20 mL vial containing 3-4 mL saturated NaCl in water. The 20 mL vials were sealed and held at 40° C. Solids were collected for XRPD analysis after one week. Form A was physically stable by XRPD after one week in humid conditions.

2.3 DVS

Figure 4:
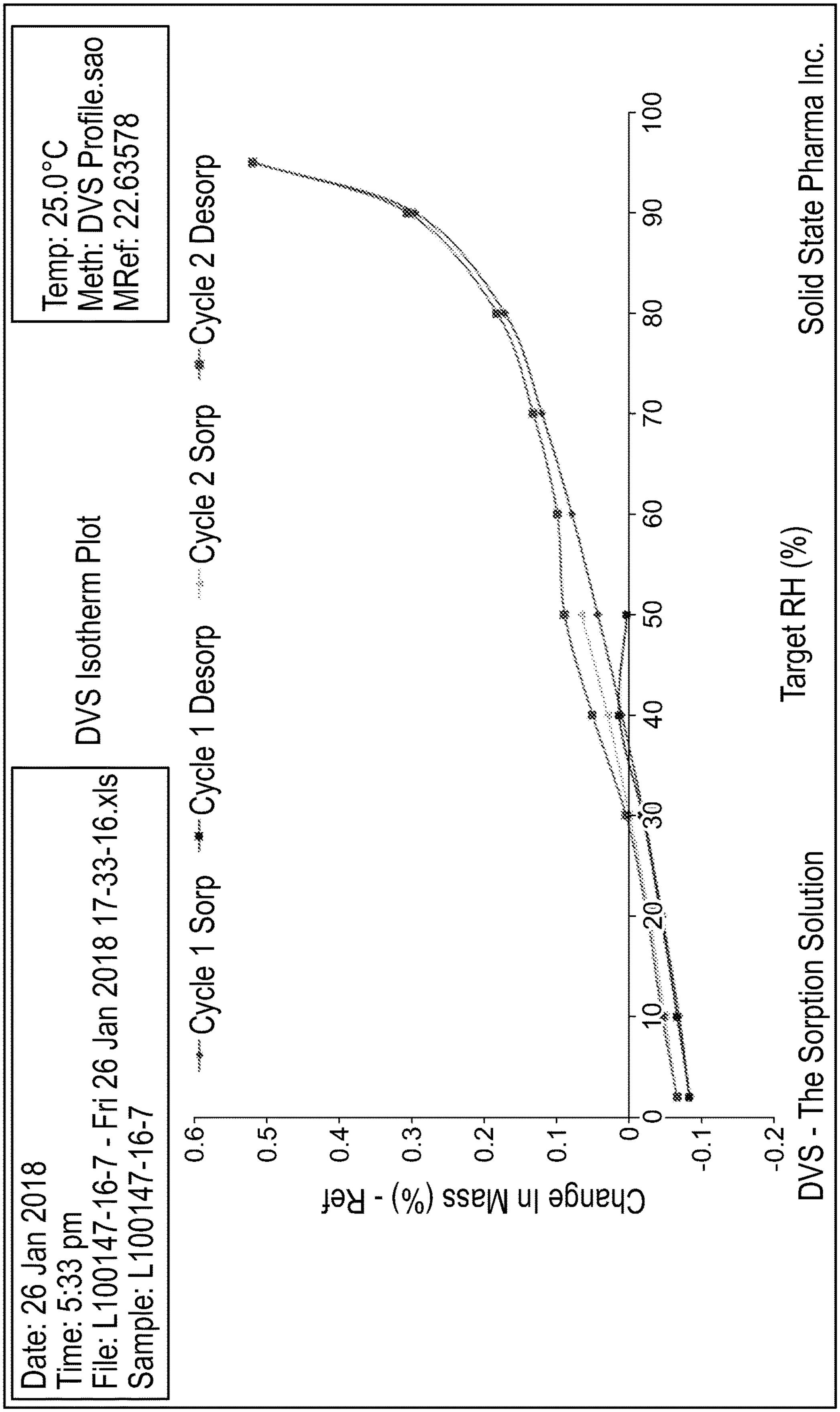
FIG. 4 shows DVS isotherms of 1.5:1 Compound (I) Sesqui-Succinate.
Figure 5:
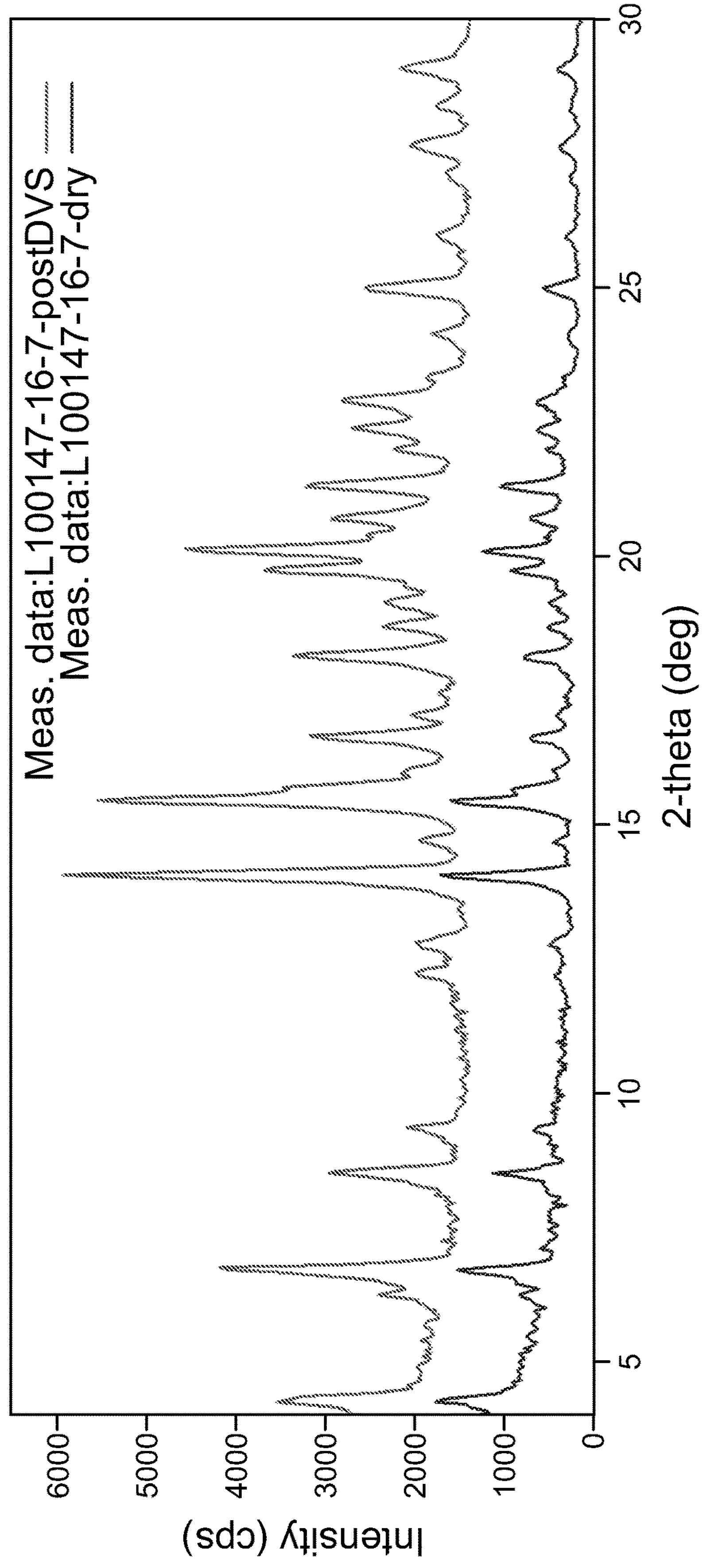
FIG. 5 shows XRPD pattern of 1.5:1 Compound (I) Sesqui-Succinate (Form A) before (bottom) and after (top) DVS measurement.

DVS showed a mass change of 0.59-0.60 wt. % between 2-95% relative humidity at 25° C. (FIG. 4). Of the mass change, 0.34-0.35 wt. % occurred above 80% relative humidity. XRPD after DVS measurement remained as Form-A (FIG. 5).

Figure 24:
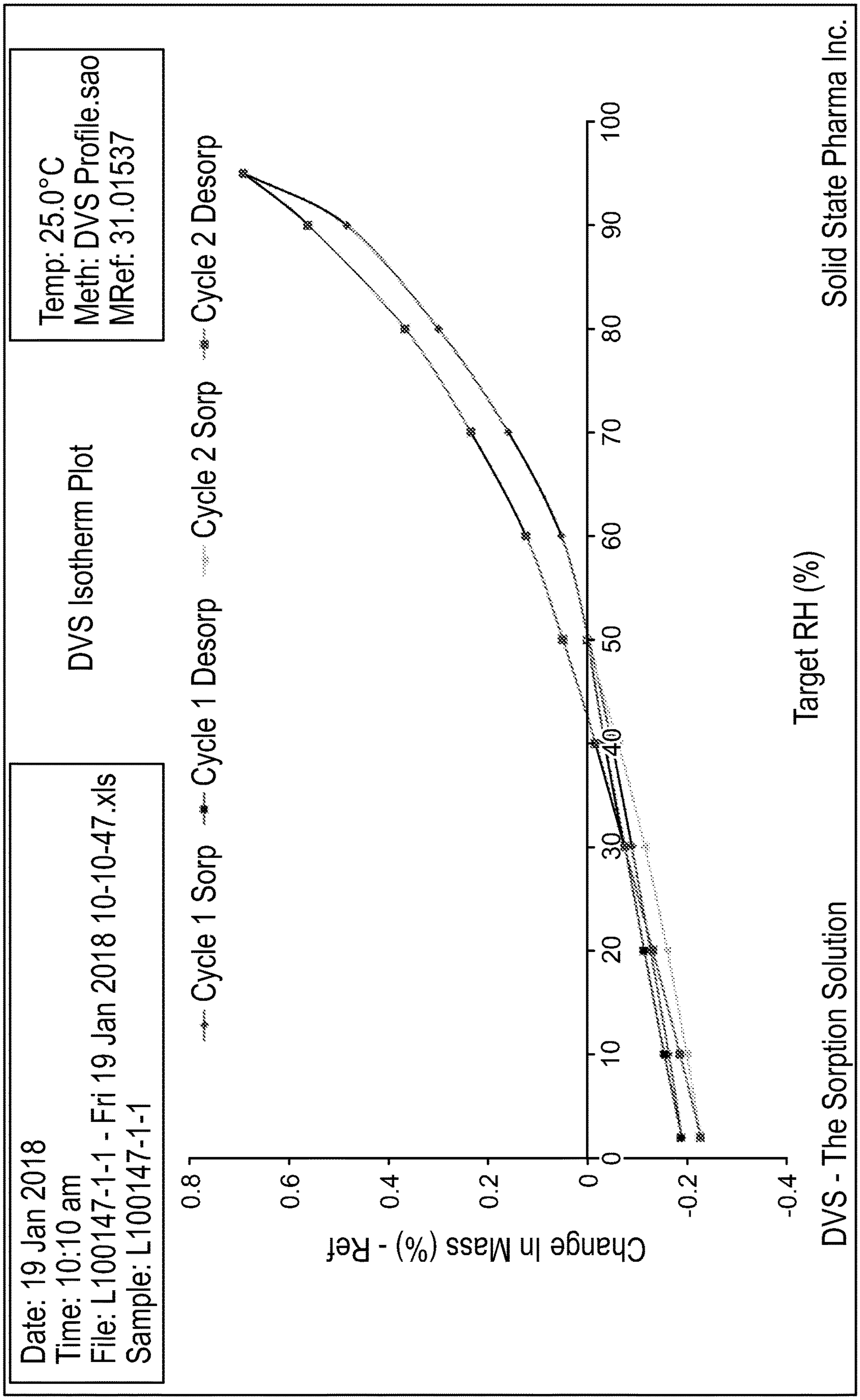
FIG. 24 shows DVS isotherms of freebase of Compound (I).

DVS was also done on the free base of Compound (I) (FIG. 24), which exhibited a reversible mass change of 0.88-0.92 wt. % between 2 and 95% relative humidity at 25° C. Of that, 0.46-0.53 wt. % of the mass change occurred above 70% relative humidity.

2.4 VT-XRPD and VH-XRPD

Figure 6:
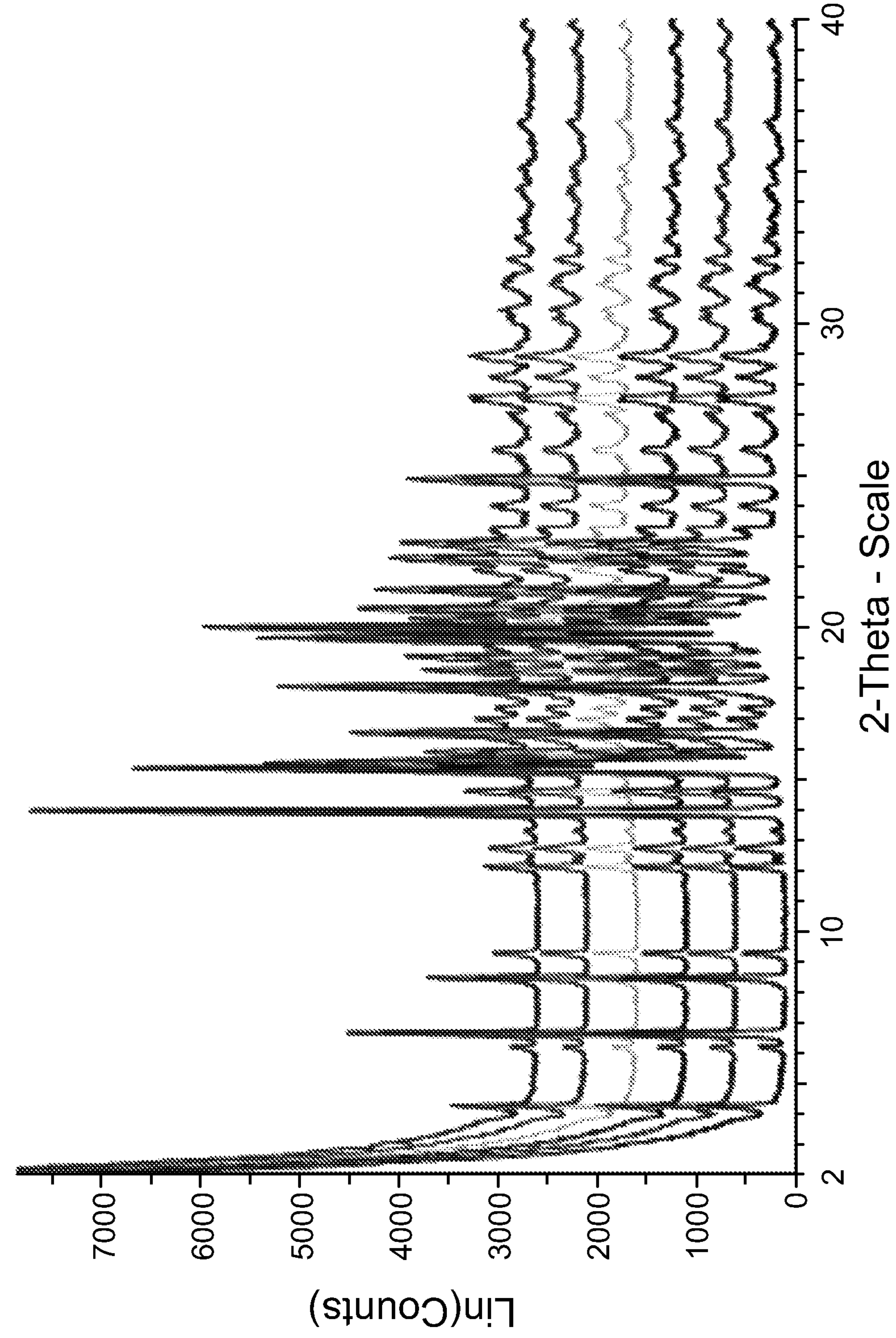
FIG. 6 shows variable humidity XRPD patterns of 1.5:1 Compound (I) Sesqui-succinate (Form A). From the bottom to the top, each XRPD diffractogram acquired in-situ on a variable humidity stage at 40% RH, 60% RH, 90% RH, 40% RH, 0% RH, and back to 40% RH.

Variable humidity experiments on Compound (I) Sesqui-Succinate salt Form A conducted using XRPD show that no change in the crystalline structure is observed with humidity (see FIG. 6).

Figure 7:
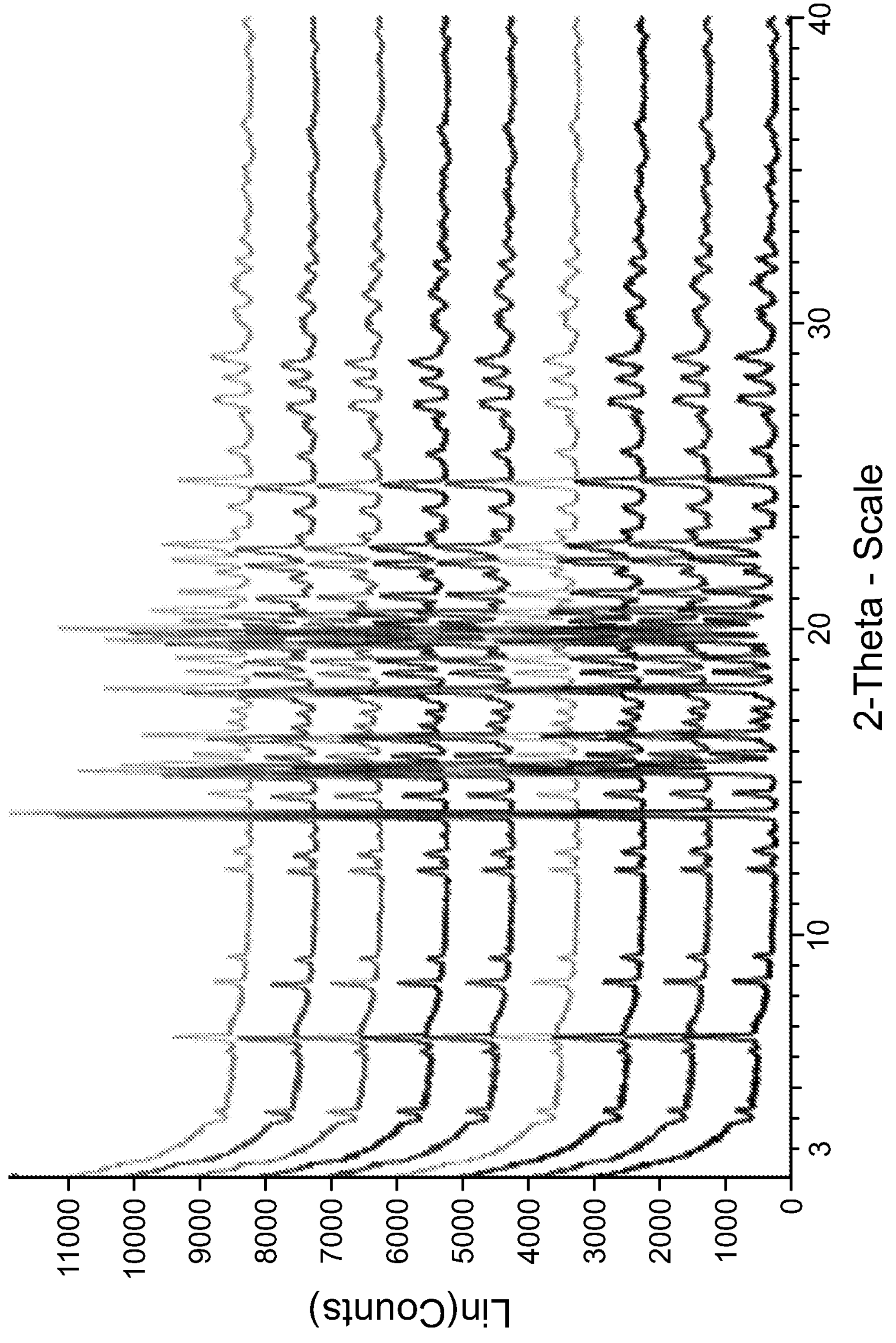
FIG. 7 shows variable temperature XRPD pattern of 1.5:1 Compound (I) Sesqui-Succinate (Form A). From the bottom to the top, each XRPD diffractogram acquired in-situ on a variable temperature stage at ambient conditions, 40° C., 60° C., 80° C., 100° C., 120° C., 140° C., 160° C., and back to 25° C.

The variable temperature experiments of Compound (I) Sesqui-Succinate salt Form A conducted using XRPD show that no change in the crystalline structure is observed below 160° C. i.e. the melting point (see FIG. 7).

Example 3: Preparations and Characterizations of 1:1 Compound (I) Crystalline HCl Salt Monohydrate 3.1 Preparations Method A:

First 25-35 mg of Compound (I) freebase was weighed into 2 mL vials. Then solvent was added to the vial (25 vol or 5 vol) followed by adding 0.9, 1.1, 1.5, 2.2, and 3.5 molar equivalents HCl stock solution in IPA.

Initially, IPA:water (9:1 vol) was added to make a total of 25 volumes (including the volume of HCl stock solution). Initially all formed solutions. The 1.1 eq. experiment showed precipitation overnight, but all others remained in solution. This may have been due to solvent composition differences, so the remaining solutions (0.9, 1.5, 2.2, and 3.5 eq.) were evaporated to dryness at 50° C. in atmosphere and then at 50° C. under active vacuum for about 3 hours. An additional experiment with 1.1 eq. was prepared in a similar manner by adding 5 vol IPA and the appropriate amount of HCl stock solution followed by evaporation to dryness at 50° C. under weak vacuum and then at 50° C. under active vacuum for about 3 hours.

To the evaporated solids, 25 volumes EtOAc was added and allowed to stir overnight at room temperature. Slurries were formed in all cases. The color of the slurries varied from a white slurry (0.9 eq.) to a vibrant/dark yellow slurry (1.5 eq. and above).

Figure 8:
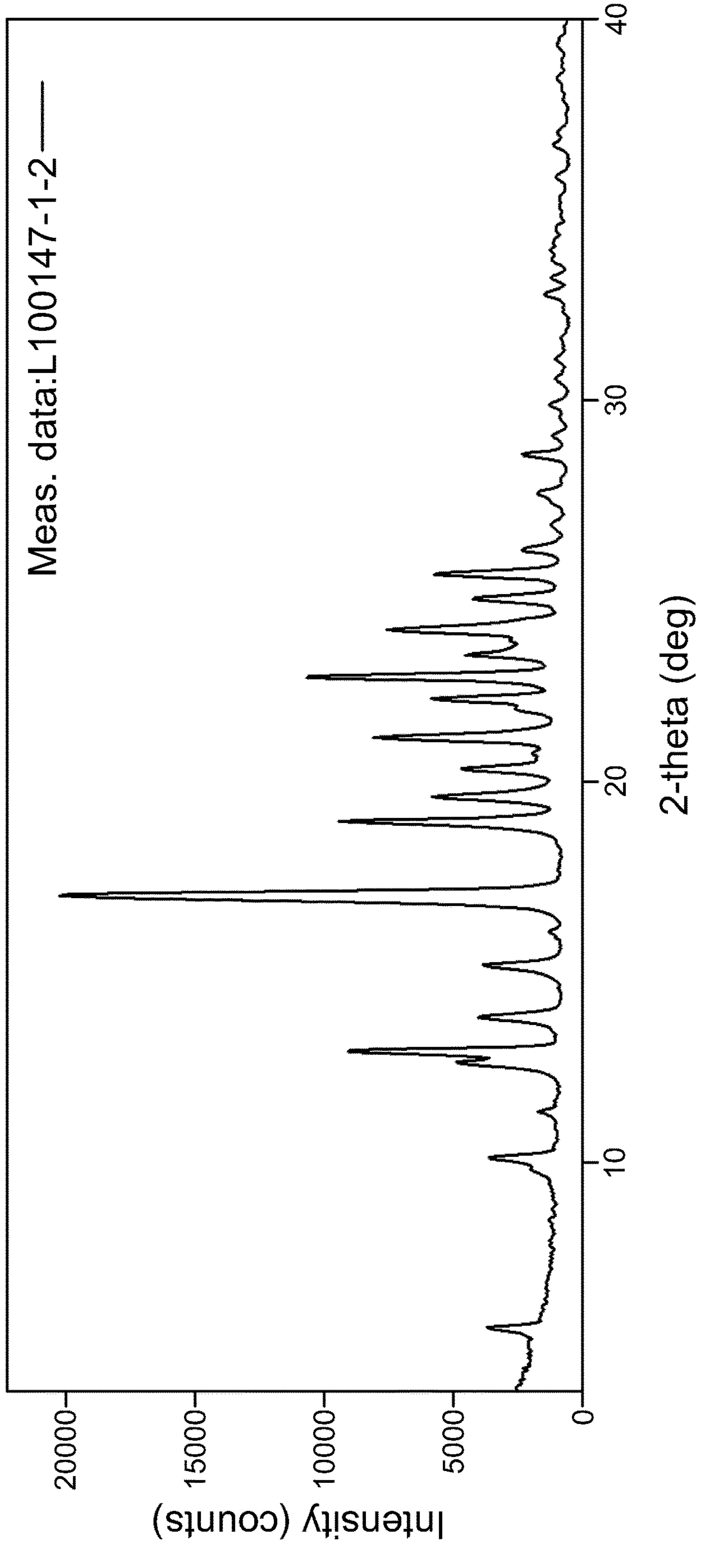
FIG. 8 shows the XRPD pattern of 1:1 Compound (I) crystalline HCl salt monohydrate (Form A).

The slurries were then filtered and solids were recovered for XRPD analysis. The salts formed with 0.9 and 1.1 eq. showed Form A (mono-HCl) by XRPD (FIG. 8). Using 1.3 and 1.5 eq. resulted in a mixture of Form A (mono-HCl) and Form B (bis-HCl). Using 2.2 and 3.5 eq. resulted in Form B (bis-HCl).

Figure 9:
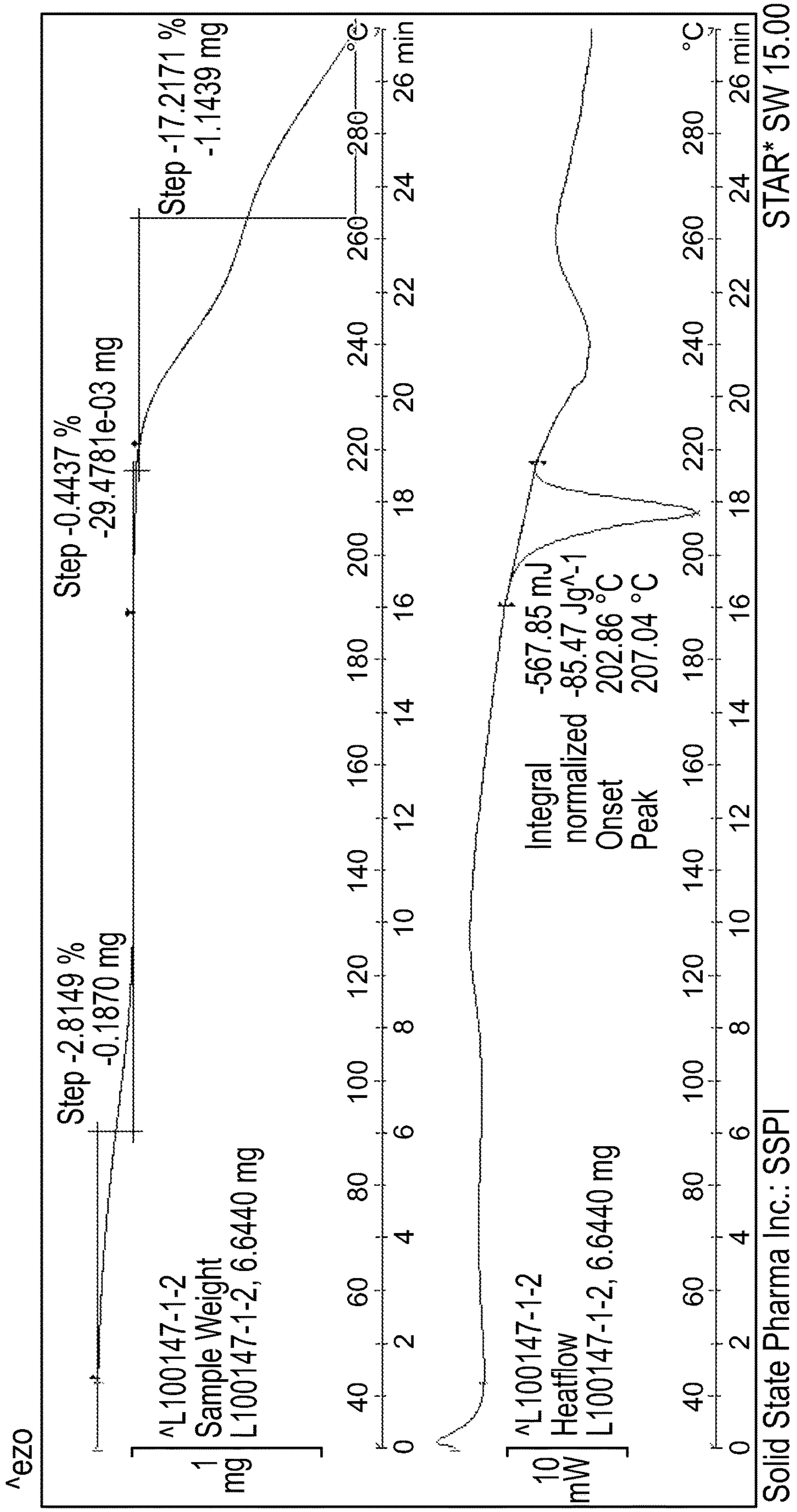
FIG. 9 shows the TGA and DSC thermograms of 1:1 Compound (I) crystalline HCl salt monohydrate (Form A).
Figure 10:
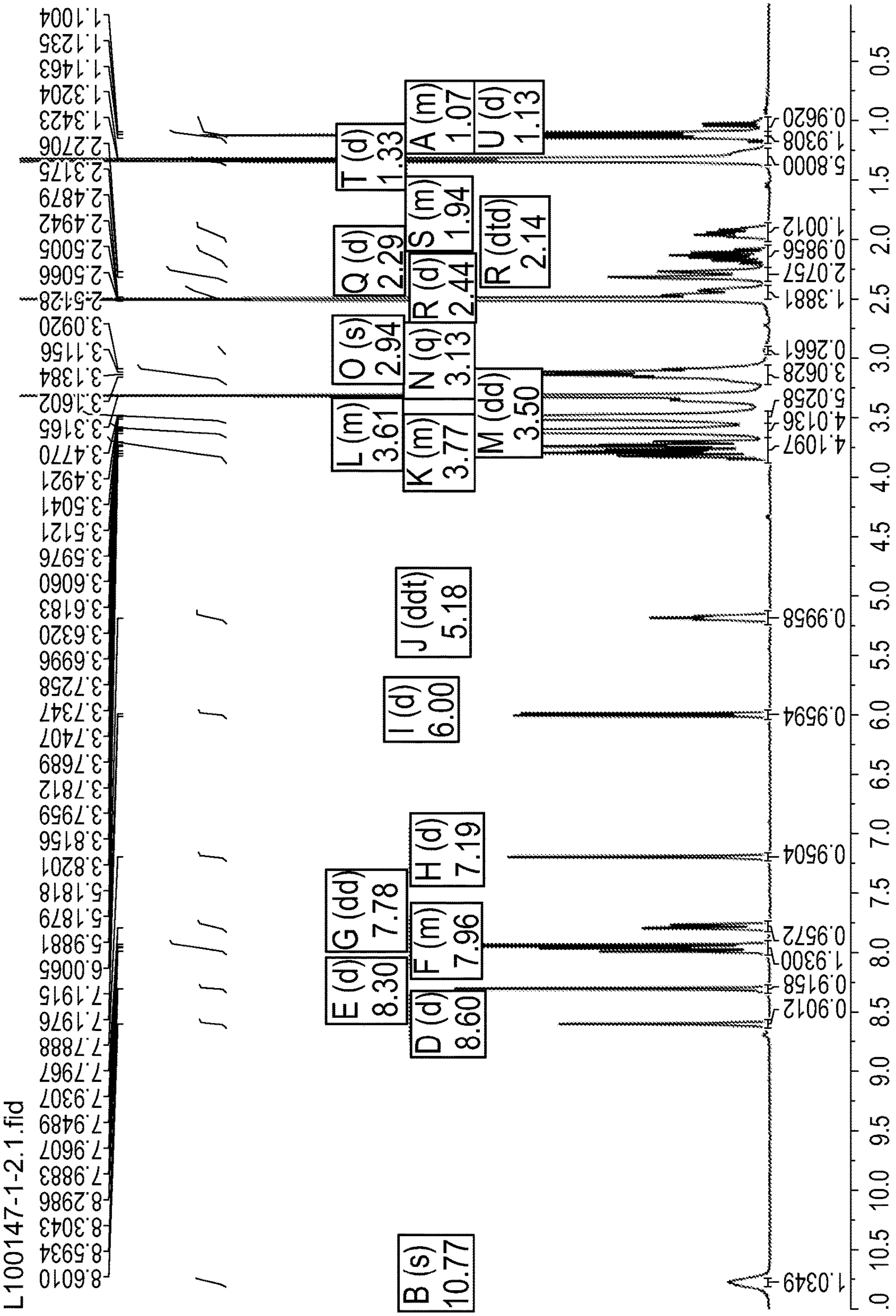
FIG. 10 shows the $^1$H-NMR of 1:1 Compound (I) crystalline HCl salt monohydrate (Form A).

The Compound (I) Crystalline HCl salt Form A was further characterized by TGA-DSC (FIG. 9), $^1$H NMR (FIG. 10), and single crystal X-ray crystallography (Table 7). The sample showed melting onset at 202.86° C. in DSC (FIG. 9). The TGA thermogram showed a mass loss of 2.81 wt. % prior to melting (associated with a very broad endotherm in DSC) and a step mass loss of 0.44 wt. % on melting. Karl Fischer titration of HCl salt showed 3.17 wt. % water, which supports that the obtained crystalline HCl salt is a monohydrate. The theoretical amount of water in a monohydrate of the HCl salt is 3.0 wt. %.

TABLE 7

Peak list for XRPD pattern of 1:1 Compound (I) Crystalline HCl Salt Monohydrate (Form A)

| 2θ (degrees) | d-spacing (angstrom) | Relative Intensity (%) |
|---|---|---|
| 5.69 | 15.53 | 8 |
| 10.14 | 8.72 | 15 |
| 12.63 | 7.00 | 11 |
| 12.91 | 6.85 | 42 |
| 13.79 | 6.42 | 16 |
| 15.14 | 5.85 | 16 |
| 17.02 | 5.21 | 100 |
| 18.98 | 4.67 | 33 |
| 19.59 | 4.53 | 21 |
| 20.32 | 4.37 | 14 |
| 21.12 | 4.20 | 28 |
| 22.17 | 4.01 | 14 |
| 22.76 | 3.90 | 35 |
| 23.35 | 3.81 | 17 |
| 23.98 | 3.71 | 36 |
| 24.80 | 3.59 | 11 |
| 25.47 | 3.49 | 17 |
| 26.12 | 3.41 | 5 |
| 28.58 | 3.12 | 6 |

Method B:

Freebase of Compound (I) (4.3 kg) was dissolved in isopropyl acetate (5.5 volumes) and isopropyl alcohol (2.5 volumes). The mixture was heated to reflux and HCl (16.5%-w/w in water, 0.95 equiv) charged over 0.75 h. After refluxing 1 h, the solution was cooled to 20-25° C. over 2 h and held 0.5 h. The crystalline product was isolated by filtration and washed with an IPAc, IPA, and water mixture to give 1:1 Compound (I) Crystalline HCl Salt Monohydrate, Form A.

3.2 Humidity Exposure

HCl salt Monohydrate Form A was placed at 40° C./75% relative humidity for one week. About 10 mg sample was placed in a 4 mL vial covered with a Kimwipe®. The vial was then placed inside a 20 mL sealed vial containing saturated aqueous sodium chloride. Some minor peak shifts were observed in the XRPD after one week humidity exposure. The peaks shifts were also observed in the XRPD patterns of some long term slurries, indicating that HCl salt Monohydrate Form A is a channel hydrate and it is possible that the peak shifts are due to variance in water content.

The day of sampling from one week humidity exposure (75% RH and 40° C.) was low humidity (<25% RH) in the laboratory.

The solid was sampled again after sitting in a sealed vial (ambient conditions) for 14 days. The solids were 1:1 Compound (I) Crystalline HCl Salt Monohydrate (Form A) by XRPD.

3.3 DVS of HCl Salt Monohydrate Form A

Figure 11:
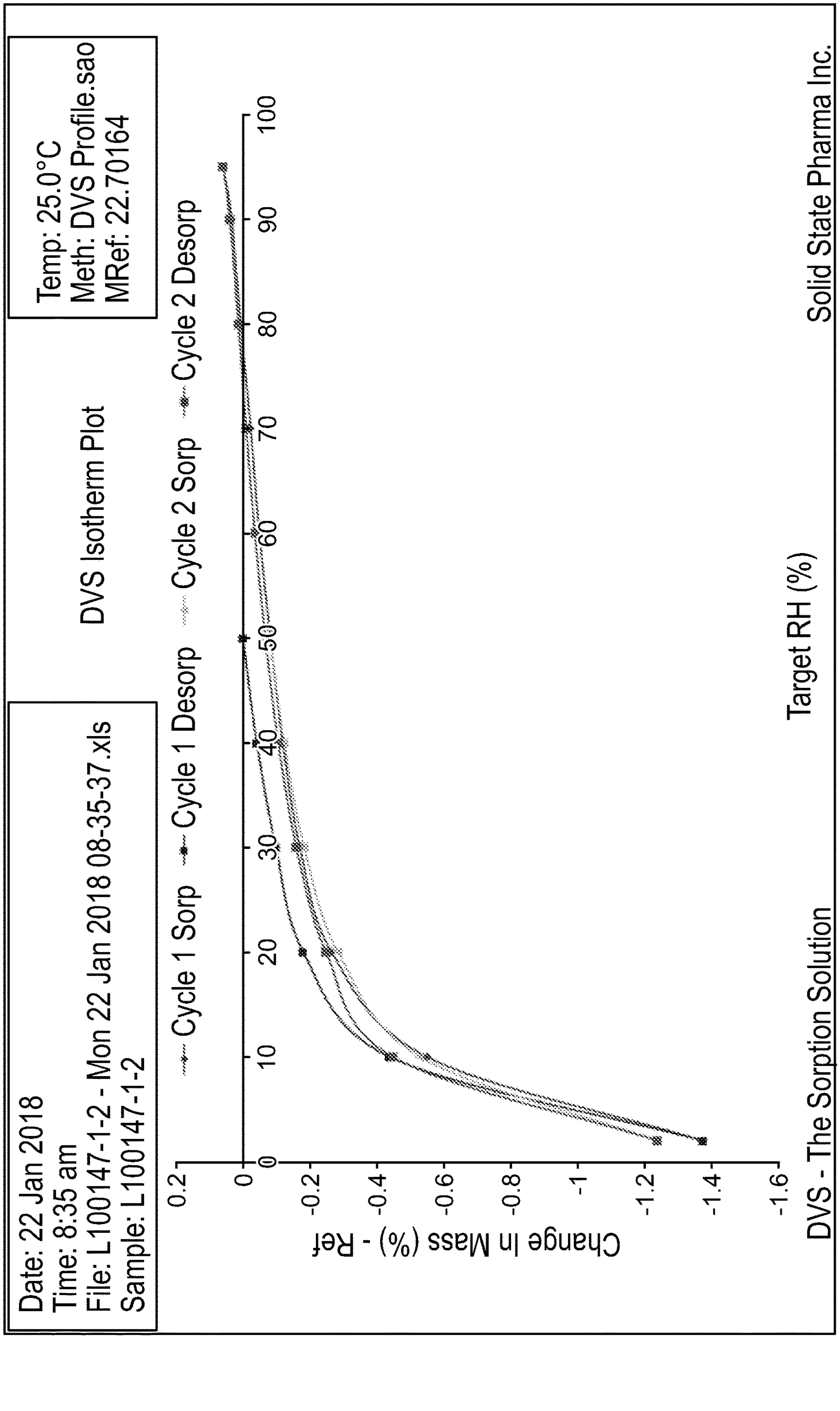
FIG. 11 shows DVS isotherms of 1:1 Compound (I) crystalline HCl salt monohydrate (Form A).

DVS was done on the HCl salt Monohydrate Form A (FIG. 11). It exhibited a mass change of 1.30-1.43 wt. % between 2 and 95% relative humidity at 25° C. Of that, 0.99-1.11 wt. % of the mass change occurred below 20% relative humidity.

Figure 12:
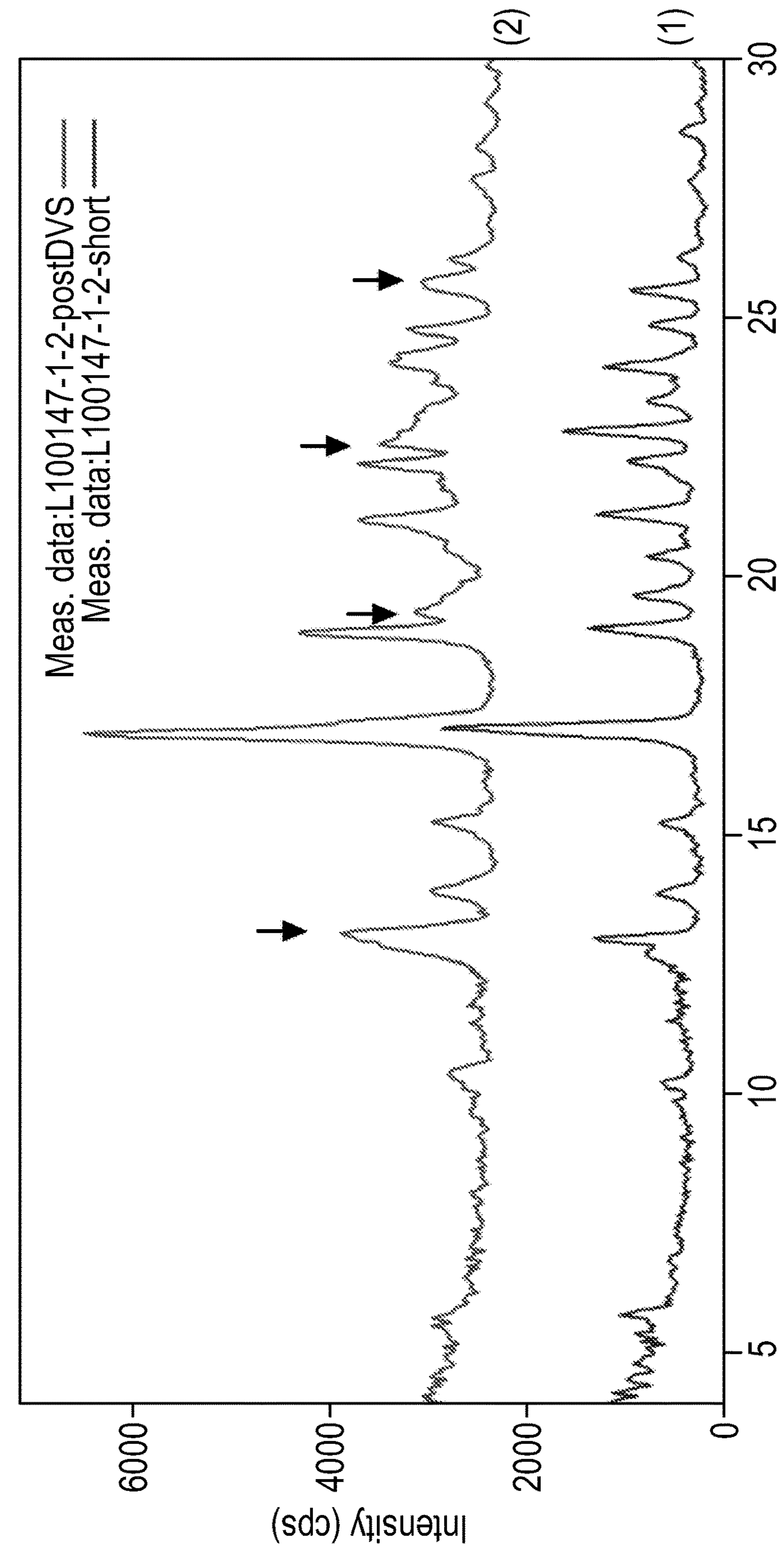
FIG. 12 shows XRPD pattern of 1:1 Compound (I) crystalline HCl salt monohydrate (Form A) before (bottom) and after (top) DVS measurement. Extra peaks observed after DVS indicated with arrows.

XRPD of the sample was analyzed after the DVS measurement (FIG. 12). All peaks of HCl salt Monohydrate Form A were present in the XRFD, but extra peaks were observed.

3.4 VT-XRPD and VH-XRPD

Figure 13:
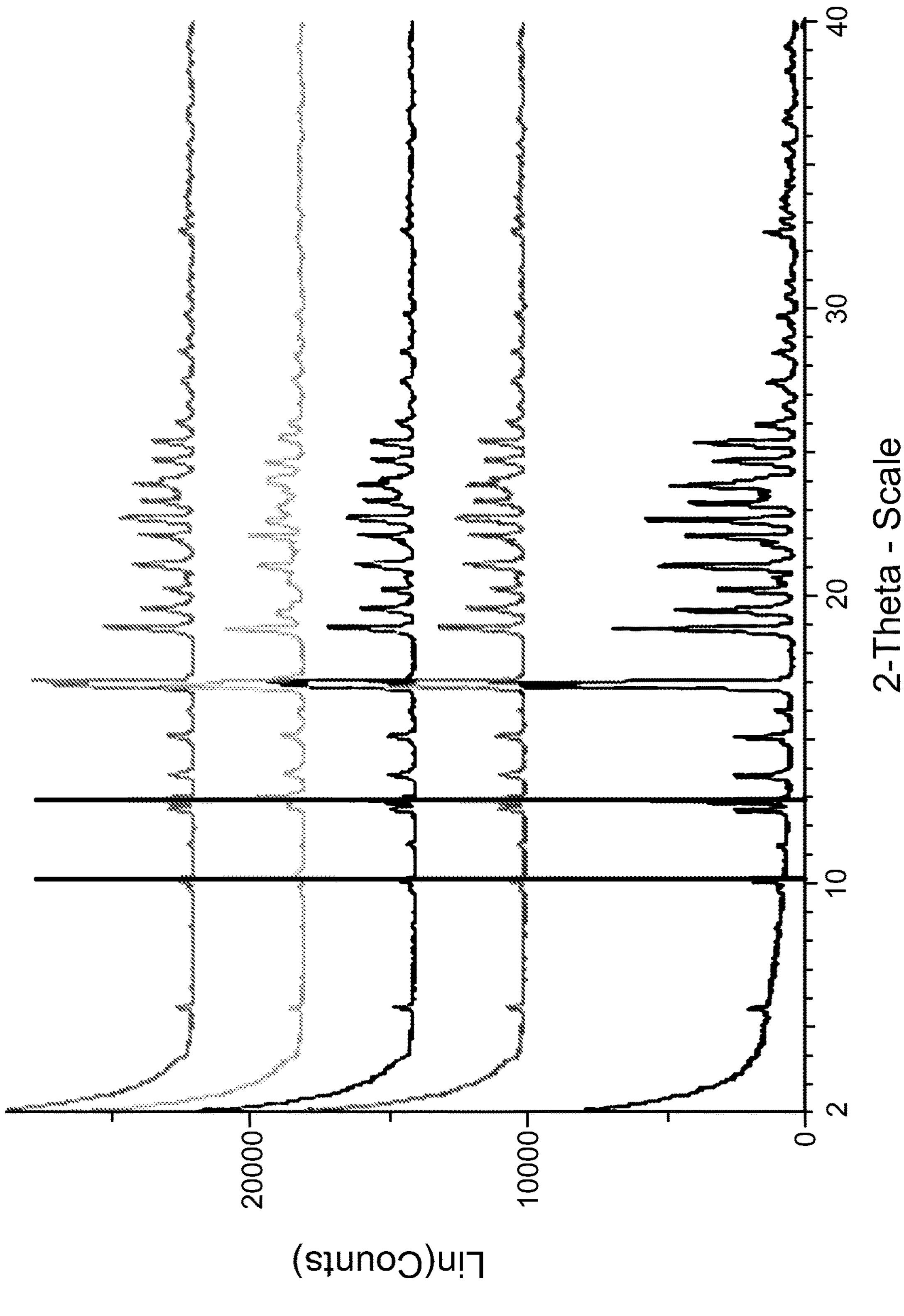
FIG. 13 shows variable humidity XRPD pattern of 1:1 Compound (I) crystalline HCl salt monohydrate (Form A). From the bottom to the top, each XRPD diffractogram acquired in-situ on a variable humidity stage at ambient conditions, 40% RH, 90% RH, 0% RH, and back to 40% RH).

The variable humidity experiments done on HCl salt Monohydrate Form A conducted using XRPD are shown in FIG. 13. The small shift observed at 0% RH towards higher angles, i.e. lower d-spacings, in the peaks at about 10 and 13° (2θ) is consistent with the crystal structure contracting following the loss of water and therefore consistent with a channel hydrate.

Figure 14:
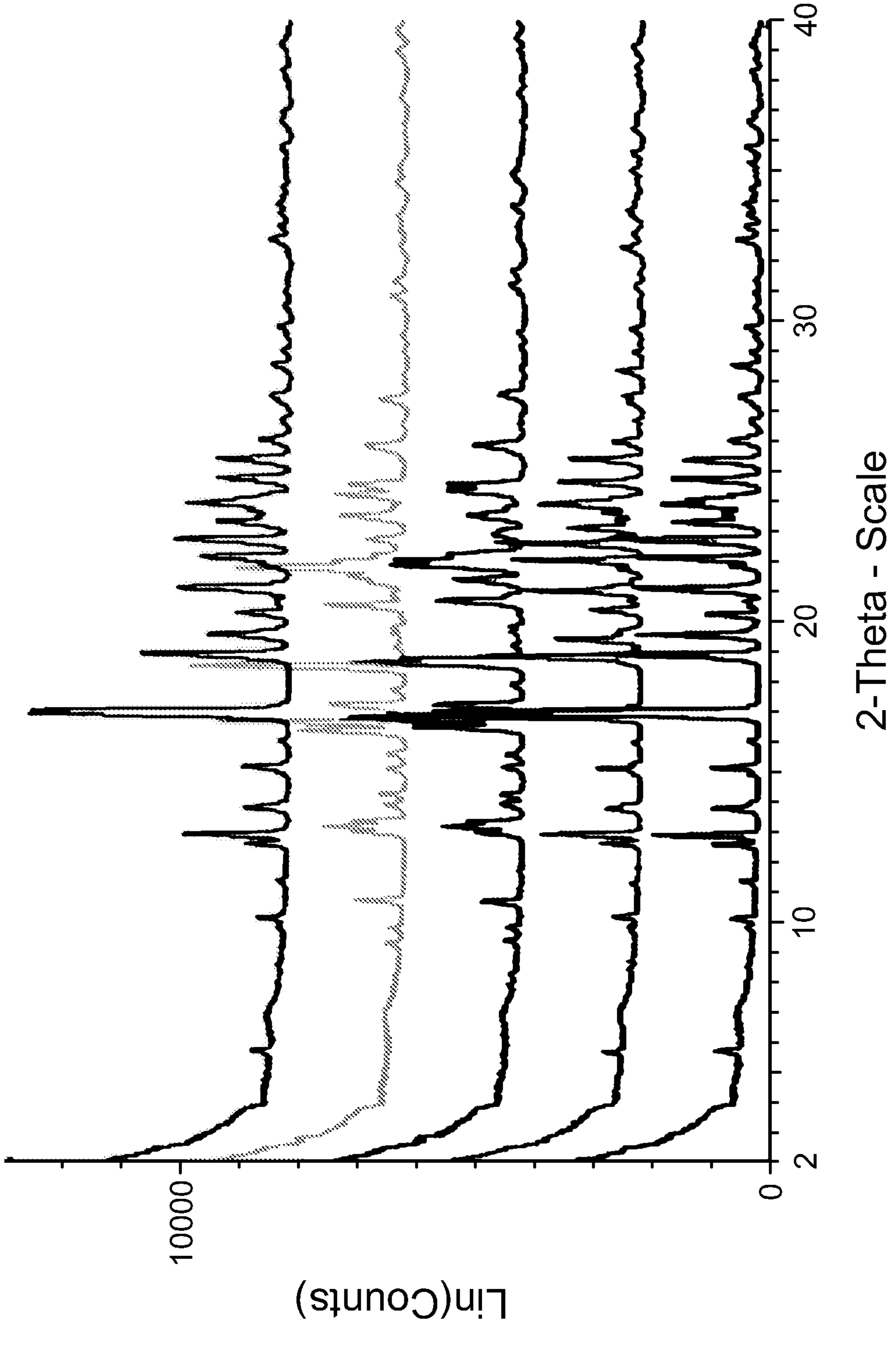
FIG. 14 shows variable temperature XRPD pattern of 1:1 Compound (I) crystalline HCl salt monohydrate (Form A). From the bottom to the top, each XRPD diffractogram acquired in-situ on a variable temperature stage at ambient conditions, 50° C., 100° C., 160° C., and back to 25° C.

The variable temperature experiments conducted using XRPD shown in FIG. 14. It confirms that the changes observed at and above 100° C. in the diffractograms are essentially due to thermal expansion as well as contraction of the unit cell due to the removal of the water molecule. The crystalline structure does not appear to collapse and/or re-arrange as in the presence of bound water/water of crystallization, this again being consistent with a channel hydrate.

3.5 Exposure to Dry Conditions and Re-Humidification

The 1:1 Compound (I) Crystalline HCl salt Monohydrate obtained from Example 3.1 was exposed to various drying conditions and then analyzed by XRPD.

The conditions were: (1) room temperature in vial containing $P_2O_5$ at 50° C., (2) 60° C. under vacuum, and (3) heating to 140° C. in DSC.

In all three cases, a new XRPD pattern was observed, which was identified as an anhydrous form of the 1:1 Compound (I) HCl salt. The relative humidity in the laboratory is sufficient to re-hydrate the sample on the bench. The DVS did not show significant mass loss until a relative humidity below 20%.

The HCl salt exposed to $P_2O_5$ at 50° C. was sampled for XRPD at the 7 day mark. The XRPD immediately after sampling showed Form D. The sample was left on the bench (22-23° C., 28% RH) for 2.25 hours and analysed by XRPD. The solid had converted to Form A. The same sample was analyzed by XRPD after sitting on the bench overnight and remained Form A by XRPD. The XRPD patterns are shown in FIG. 12.

Example 4: Preparations and Characterizations of Anhydrous 1:1 Compound (I) Crystalline HCl Salt (Form D)

4.1 Preparations

Figure 15:
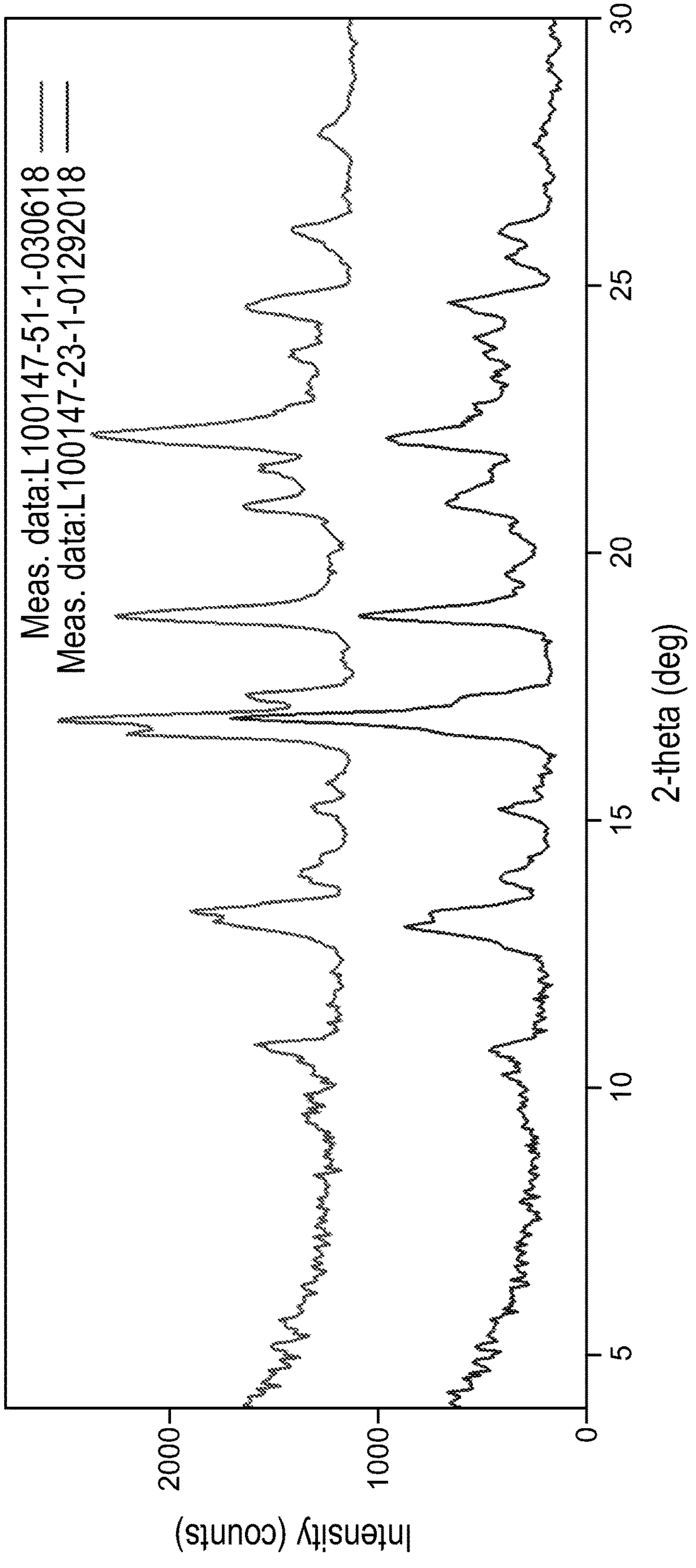
FIG. 15 shows the XRPD patterns of anhydrous 1:1 Compound (I) crystalline HCl salt (Form D) observed during initial screening (bottom) and scaled-up (top).

Anhydrous 1:1 Compound (I) Crystalline HCl Salt (Form D) was prepared by extended drying of Form A (monohydrate) in a sealed vial containing phosphorous pentoxide at 50° C. Specifically, 100 mg of the Form A (monohydrate) obtained from Example 4.1 was placed in a dry environment for 4 days. An open 4 mL vial containing the sample was placed in a sealed 20 mL vial containing $P_2O_5$ at 50° C. for two days before sampling. It was identified as a new crystalline form (Form D) by XRPD (FIG. 15).

It was observed that Form D converted to Form A upon exposure to ambient conditions (22° C., 35% RH) for 2.25 hours. Thus, characterization of Form D was done with minimal exposure to ambient conditions.

Figure 16:
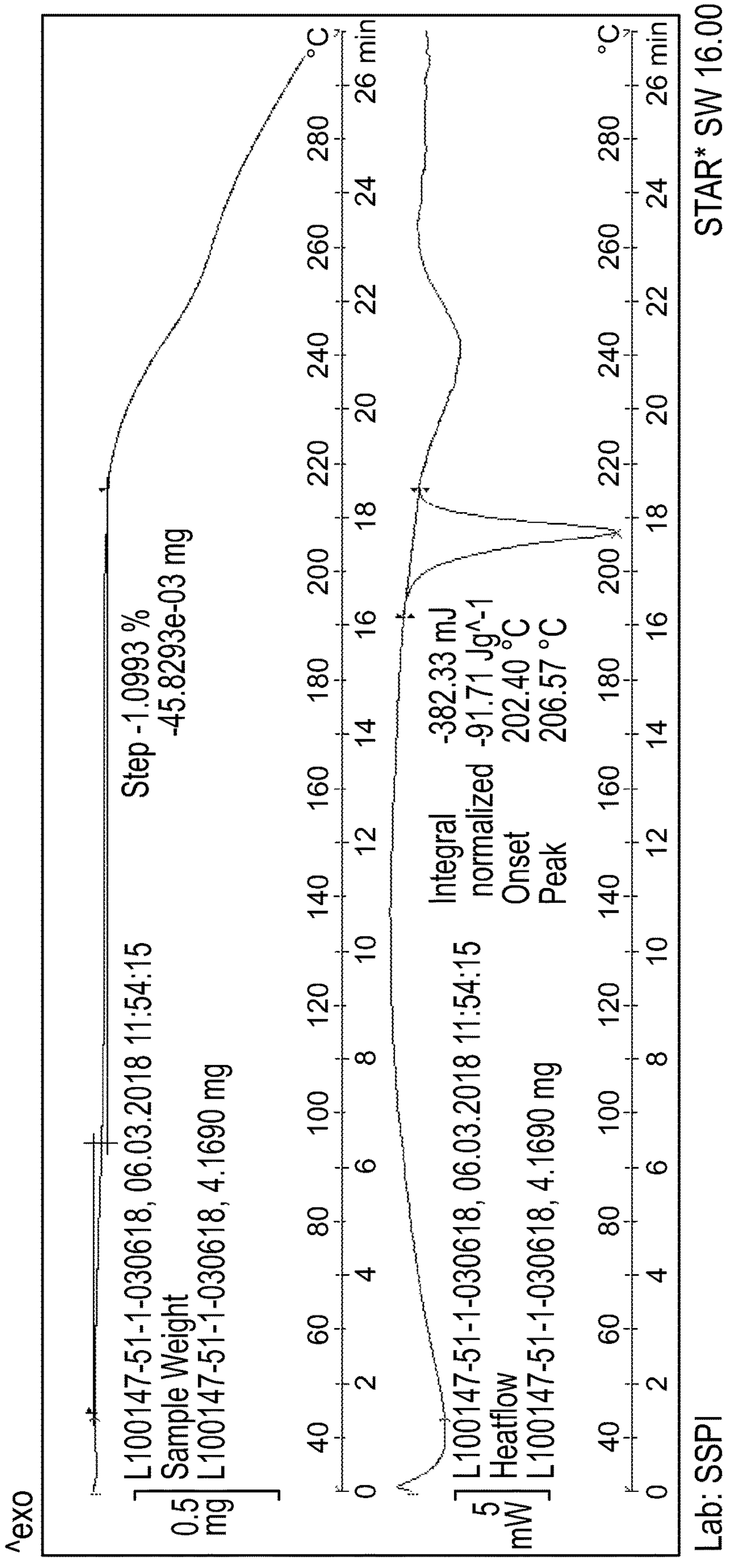
FIG. 16 shows the TGA and (DSC thermograms of anhydrous 1:1 Compound (I) crystalline HCl salt (Form D).

DSC thermogram of the Form D sample showed an endotherm onset at 202.4° C. (FIG. 16). TGA of the Form D sample showed a total mass loss of 1.10 wt. % (FIG. 16). Form A (monohydrate) also shows a DSC endotherm with onset at 202-203° C. after dehydration.

Karl Fischer titration showed a water content of 0.72 wt. % for the Form D sample. The Form D sample exhibited a cubic morphology by microscopy. The morphology did not differ significantly from the starting material (Form A). Purity of the Form D sample was 98.82 area percent by HPLC.

Form D converted to Form A (monohydrate) upon humidity exposure (>90% RH overnight and 74% RH/40° C. one week).

Figure 17:
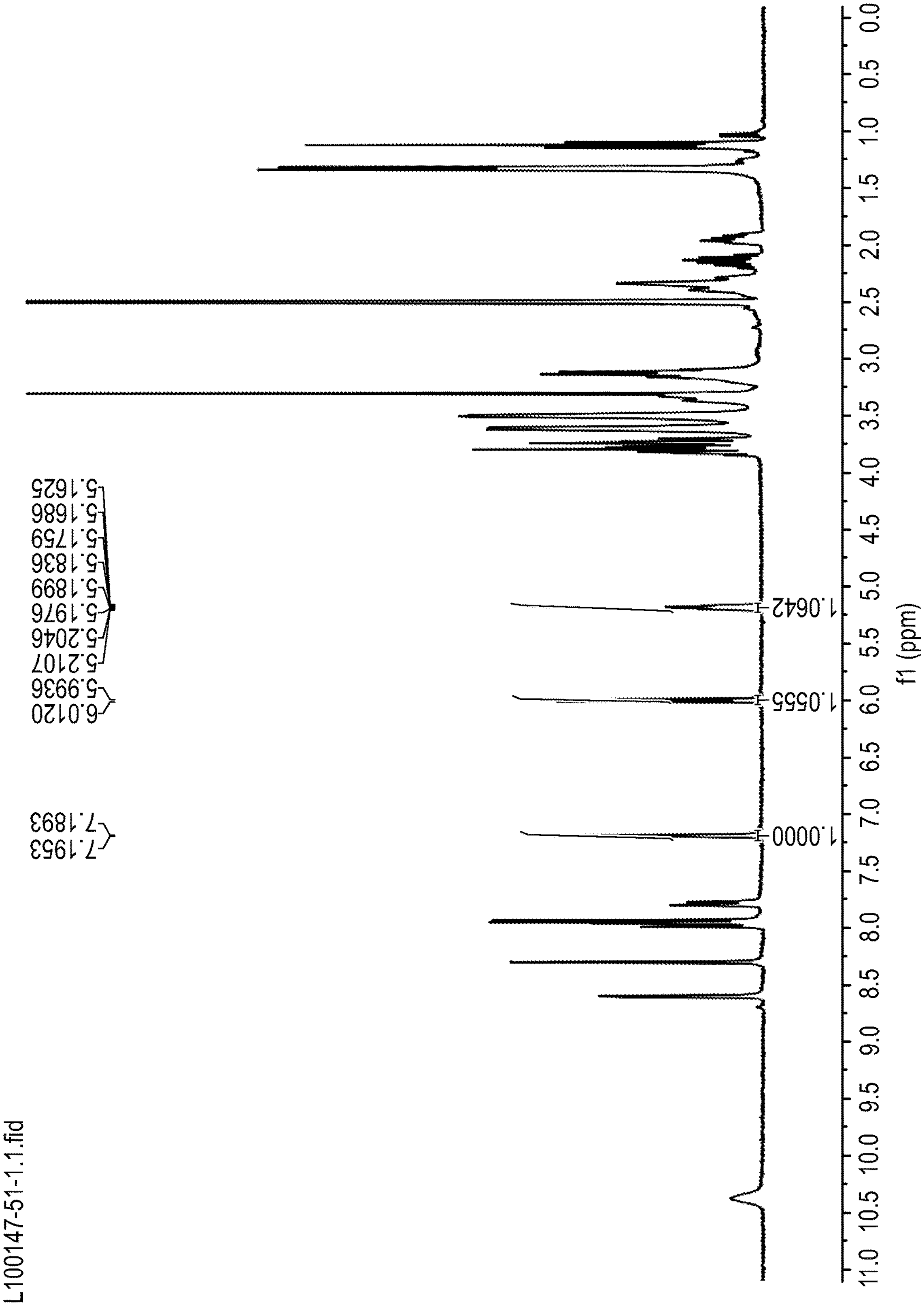
FIG. 17 shows the $^1$H-NMR of anhydrous 1:1 Compound (I) crystalline HCl salt (Form D).

The Compound (I) Crystalline HCl salt Form D was further characterized by $^1H$ NMR (FIG. 17).

TABLE 8

Peak list for XRPD pattern of Anhydrous 1:1 Compound (I) Crystalline HCl Salt (Form D).

| 2θ (degrees) | d-spacing (angstrom) | Relative Intensity (%) |
|---|---|---|
| 9.36 | 9.44 | 8 |
| 9.79 | 9.02 | 5 |
| 10.81 | 8.18 | 29 |
| 13.05 | 6.78 | 25 |
| 13.25 | 6.68 | 30 |
| 13.89 | 6.37 | 10 |
| 14.32 | 6.18 | 5 |
| 15.24 | 5.81 | 8 |
| 15.68 | 5.65 | 5 |
| 16.62 | 5.33 | 27 |
| 16.87 | 5.25 | 63 |
| 17.35 | 5.11 | 27 |
| 18.02 | 4.92 | 1 |
| 18.83 | 4.71 | 62 |
| 19.88 | 4.46 | 1 |
| 20.84 | 4.26 | 25 |
| 21.64 | 4.10 | 18 |
| 22.18 | 4.00 | 100 |
| 23.69 | 3.75 | 9 |
| 24.65 | 3.61 | 31 |
| 26.04 | 3.42 | 15 |
| 27.81 | 3.21 | 12 |

Example 5: Preparations and Characterizations of Anhydrous 1:1 Compound (I) Crystalline HCl Salt (Form G)

5.1 Preparations

Form G was observed while fast cooling from IPA solution and also from amorphous slurries in EtOAc and MtBE (low crystallinity). Form G was scaled-up by fast cooling in IPA. About 200 mg as-received HCl salt was weighed in a 20 mL vial and 60 volumes IPA was added while stirring at 50° C. Solids dissolved and the solution was transferred to a beaker of ice water (0° C.). The solution was seeded with a sample of Form G at 0° C. The seed was retained, but a thick slurry was not formed. The sample was transferred to a freezer at −20° C. where solids precipitated over the weekend.

Figure 18:
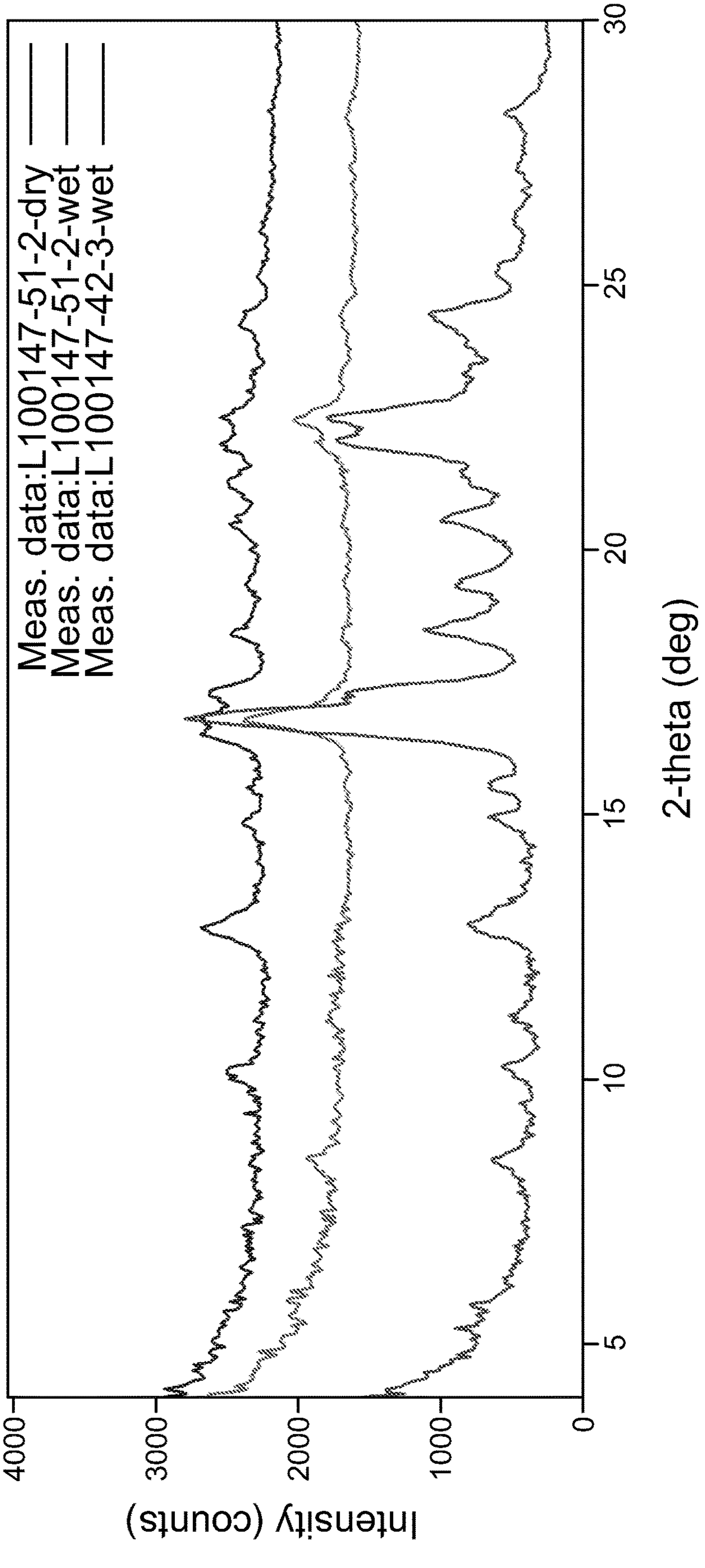
FIG. 18 shows the XRPD patterns of anhydrous 1:1 Compound (I) crystalline HCl salt (Form G) observed during screening (bottom), from scale-up (wet) (middle), and dry (top).

The resulting slurry appeared fluffy. Filtration was extremely slow and the solid was somewhat sticky. The collected solids were quite wet due to poor filtration. Collected solids were dried at 50° C. under vacuum overnight. The solids obtained from the scale-up were lower crystallinity than those observed during the screening (FIG. 18).

Figure 19:
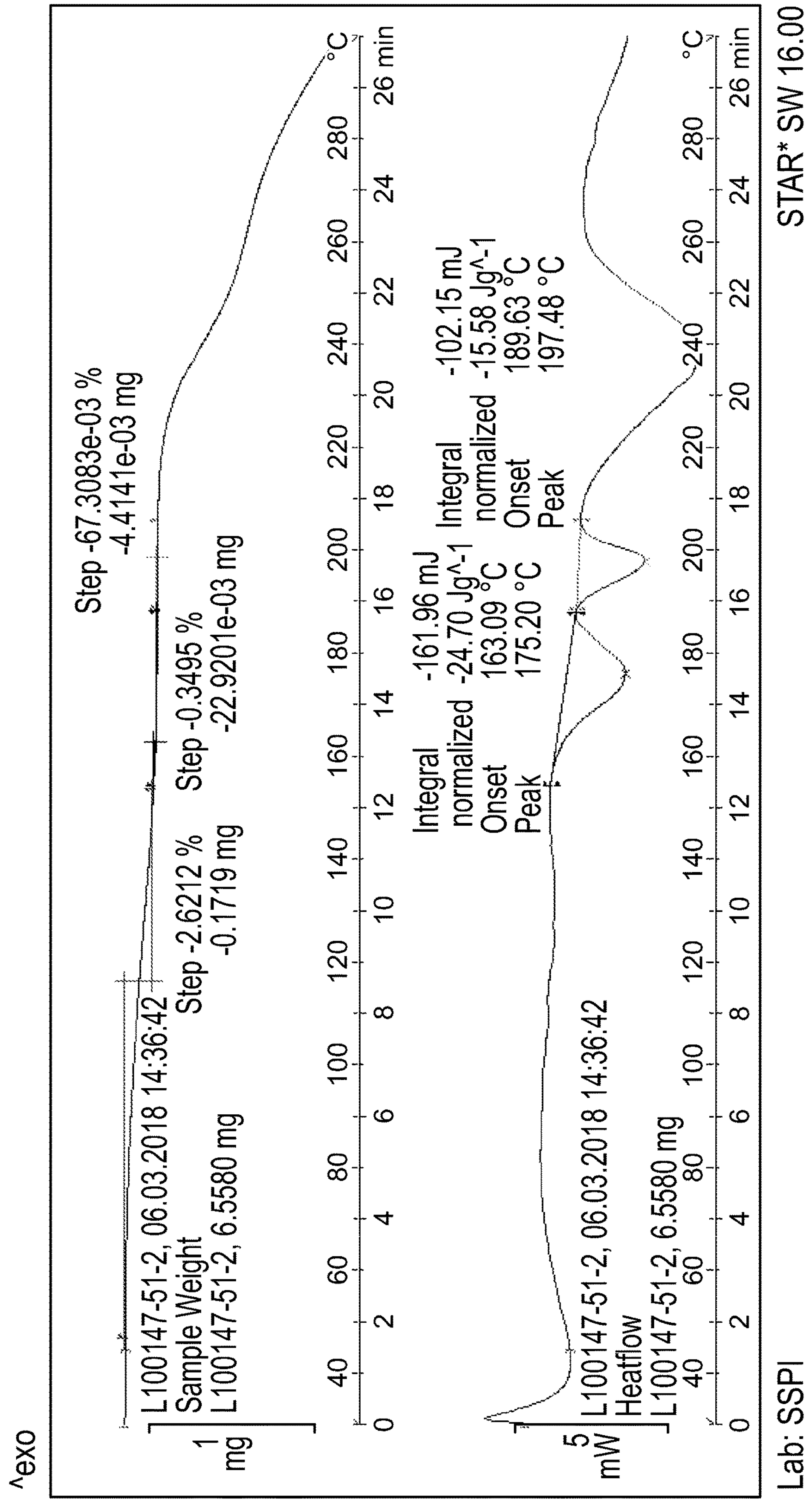
FIG. 19 shows the TGA and DSC thermograms of anhydrous 1:1 Compound (I) crystalline HCl salt (Form G).
Figure 20:
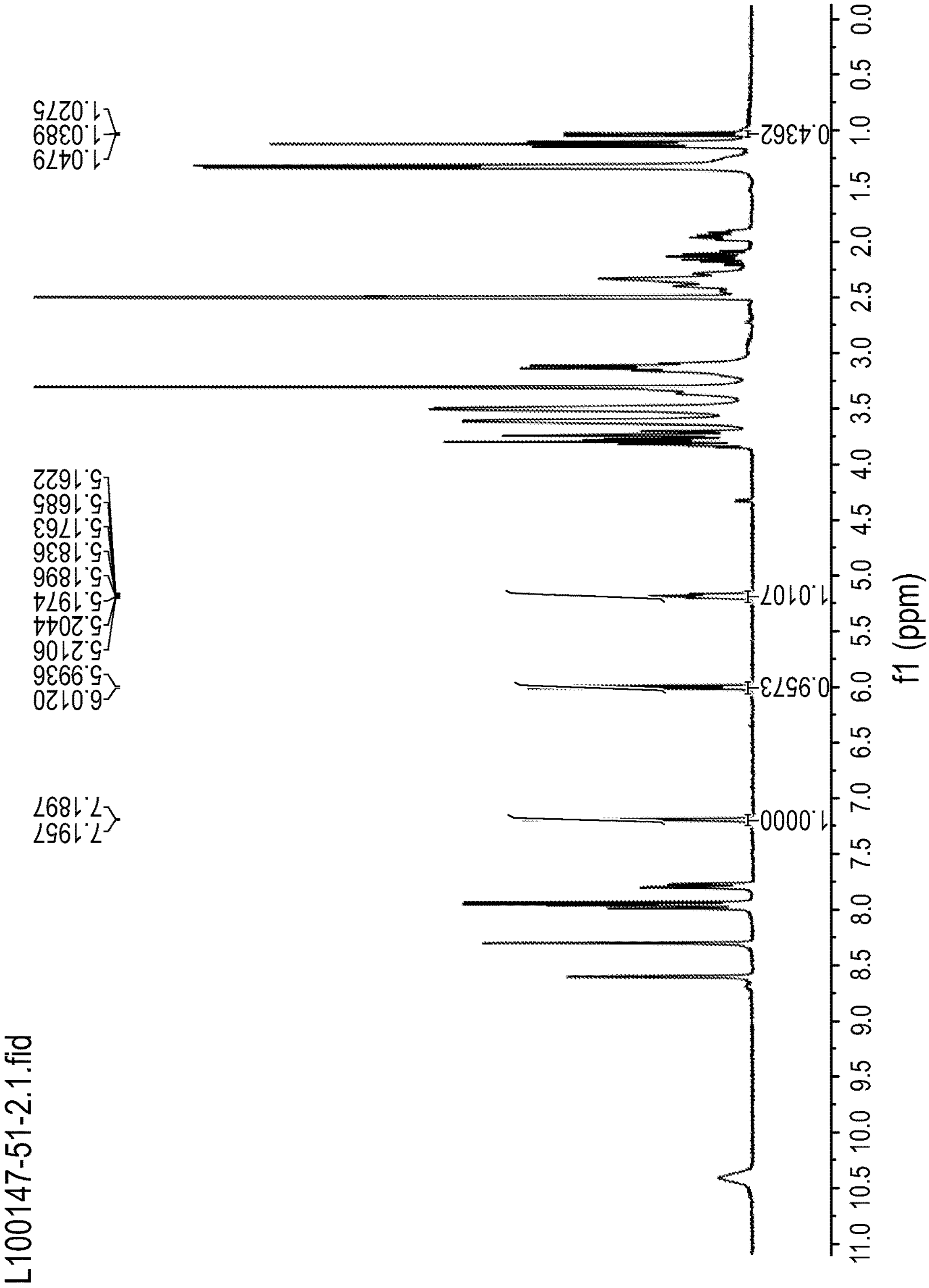
FIG. 20 shows the $^1$H-NMR of anhydrous 1:1 Compound (I) crystalline HCl salt (Form G).

A DSC thermogram of Form G shows two endotherms with onsets at 163.1° C. and 189.6° C. followed by decomposition (FIG. 19). A TGA thermogram showed a gradual initial mass loss of 2.62 wt. % prior to the first endothermic event, followed by smaller mass losses during the endothermic events (0.35 wet. % and 0.07 wt. %). Standalone DSC agrees well with the coupled DSC-TGA data and also shows a broad endotherm between 80-130° C. A Form G sample was heated in DSC to above the broad endotherm followed by cooling to room temperature. No change was observed in XRPD.

Karl Fischer titration showed a water content of 2.79 wt. % for sample.

Microscopy of the Form G sample showed chunks of solid and some irregular/fine particles. Purity of the Form G sample was 98.89 area percent by HPLC.

A Form G sample partially converted to Form A overnight in a high humidity environment (>90% RH). Form G was stable (by XRPD) after one week humidity exposure (75% RH/40° C.).

TABLE 9

Peak list for XRPD pattern of Anhydrous 1:1 Compound (I) Crystalline HCl Salt (Form G).

| 2θ (degrees) | d-spacing (angstrom) | Relative Intensity (%) |
|---|---|---|
| 10.19 | 8.67 | 38 |
| 12.84 | 6.89 | 73 |
| 14.88 | 5.95 | 14 |
| 15.50 | 5.71 | 10 |
| 16.65 | 5.32 | 100 |
| 17.35 | 5.11 | 39 |
| 18.43 | 4.81 | 17 |
| 19.37 | 4.58 | 4 |
| 20.00 | 4.44 | 1 |
| 20.51 | 4.33 | 19 |
| 21.25 | 4.18 | 26 |
| 22.02 | 4.03 | 23 |
| 22.49 | 3.95 | 47 |
| 24.25 | 3.67 | 25 |
| 25.25 | 3.52 | 5 |
| 26.04 | 3.42 | 4 |
| 28.22 | 3.16 | 7 |

Example 6: Preparations and Characterizations of Anhydrous 1:1 Compound (I) Crystalline HCl Salt (Form I)

6.1 Preparations

Form I was observed when doing salt formation experiments in anhydrous solvent systems (MtBE:IPA and cyclohexane:IPA). Form I was scaled-up by carrying out salt formation in cyclohexane:IPA. First about 200 mg freebase of Compound (I) was weighed in a 4 mL vial and 15 volumes cyclohexane was added to form a slurry. 1.1 molar equivalents of HCl were added as a 0.55 M solution in IPA over 30 minutes. The HCl solution was dispensed dropwise in three aliquots. After the first aliquot, a yellow slurry formed followed by gumming. Gumming remained upon addition of the final two aliquots. The vial was then heated to 45° C., held one hour, and seeded with a Form I sample. After seeding the sample was cooled naturally to room temperature. After seeding, white solid was observed and after cooling to room temperature the sample was largely a white slurry with some yellow gum on the vial walls. The slurry was filtered and washed twice with two volumes cyclohexane.

Figure 22:
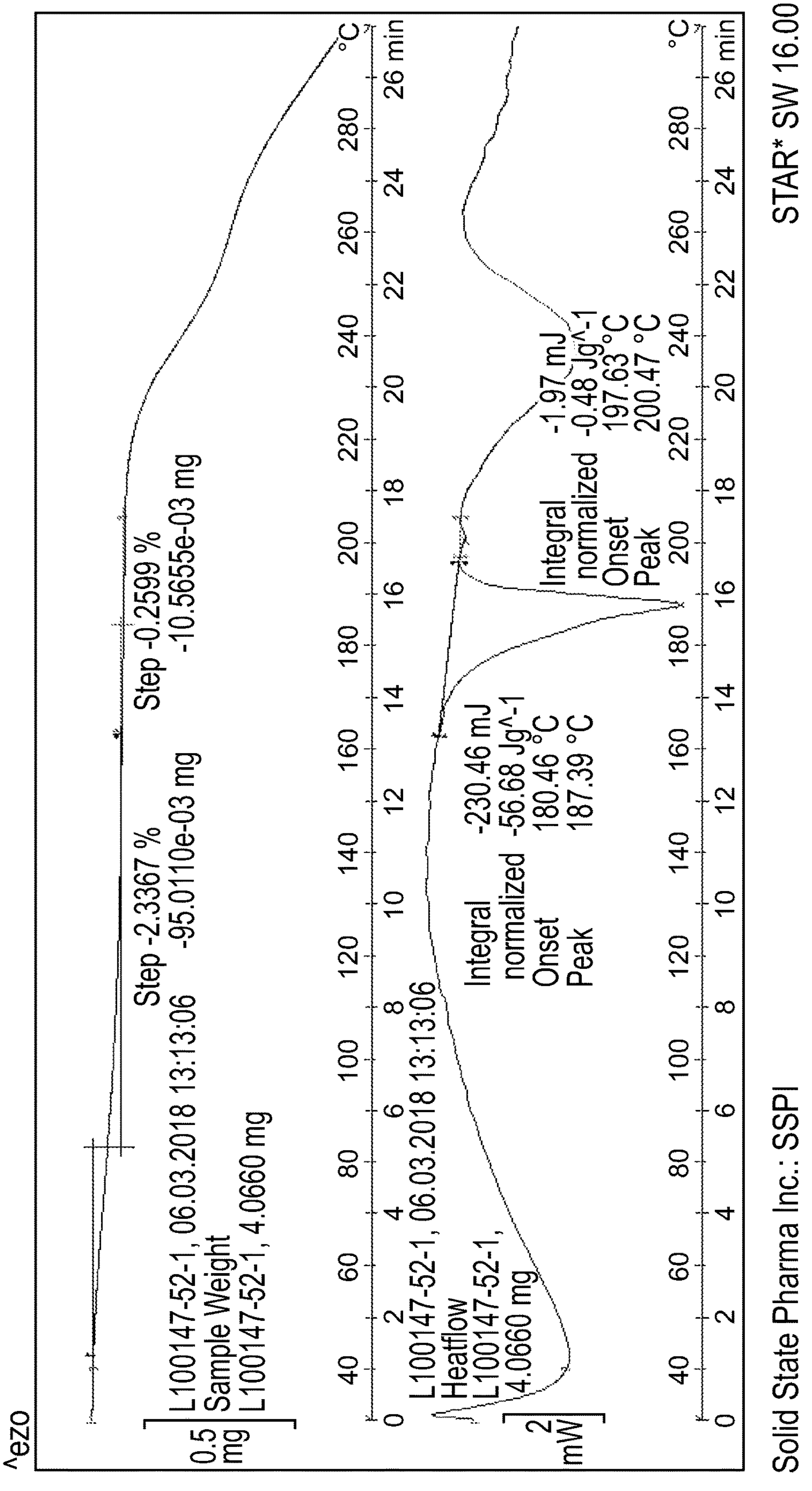
FIG. 22 shows the TGA and DSC thermograms of anhydrous 1:1 Compound (I) crystalline HCl salt (Form I).
Figure 23:
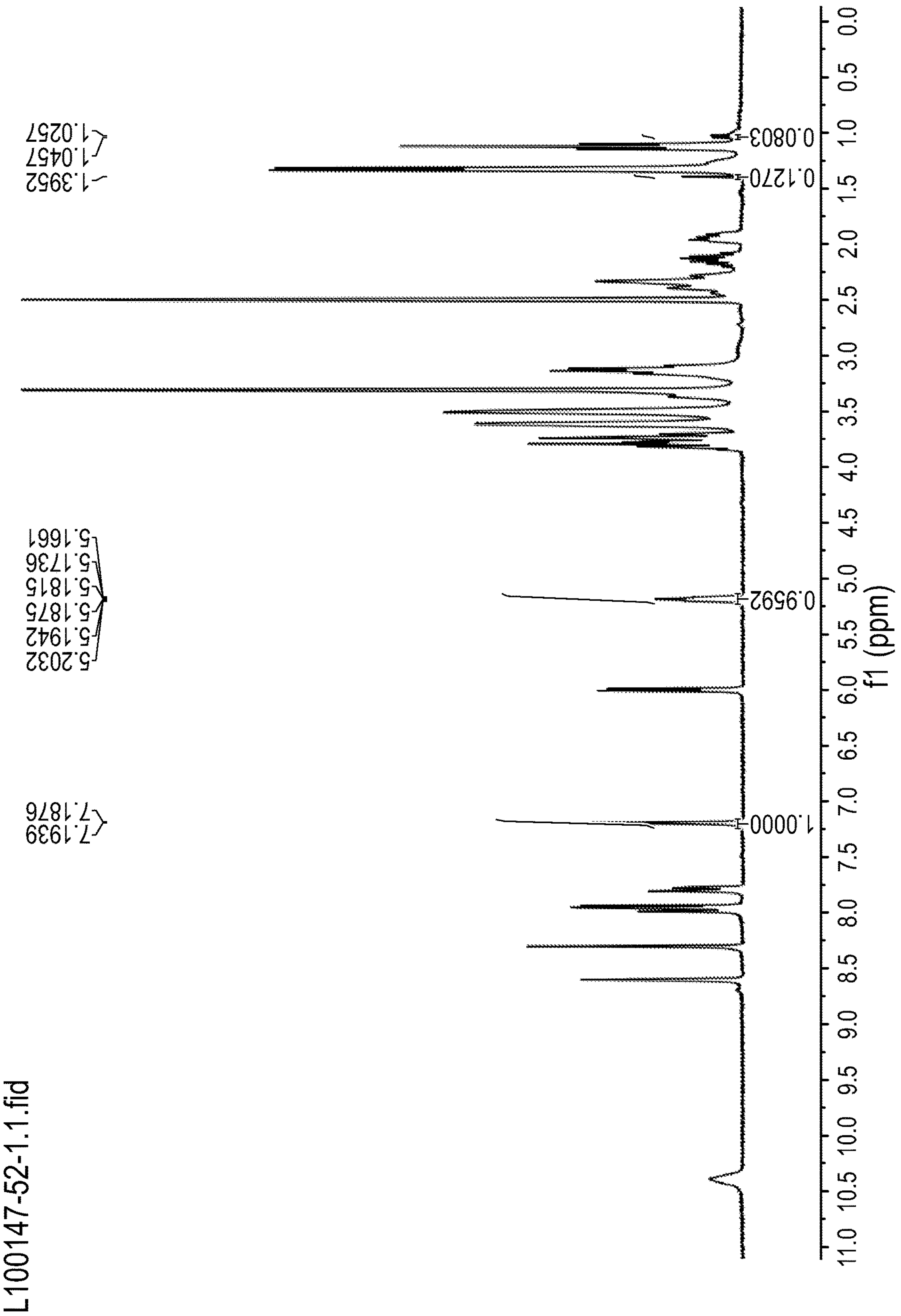
FIG. 23 shows the ($^1$H-NMR of anhydrous 1:1 Compound (I) crystalline HCl salt (Form I).

The DSC thermogram of a Form I sample shows an endotherm with onset at 180.5° C. followed by a small endotherm with onset at 198° C. (FIG. 22). The TGA thermogram shows a gradual mass loss prior to melting of 2.34 wt. % and a mass loss of 0.26 wt. % on melting.

Standalone DSC agrees well with the coupled DSC-TGA data and also shows an endotherm between 90-120° C. A Form I sample was heated to 150° C. in DSC followed by cooling to room temperature for XRPD analysis. There was no change observed in the XRPD pattern. All peaks are shifted to a slightly higher two theta, which should be due to sample displacement.

Karl Fischer titration showed a water content of 2.64 wt. % for sample Form I.

Microscopy showed fines (needles) and agglomerates. Purity of Form I was 99.51 area percent by HPLC.

Figure 21:
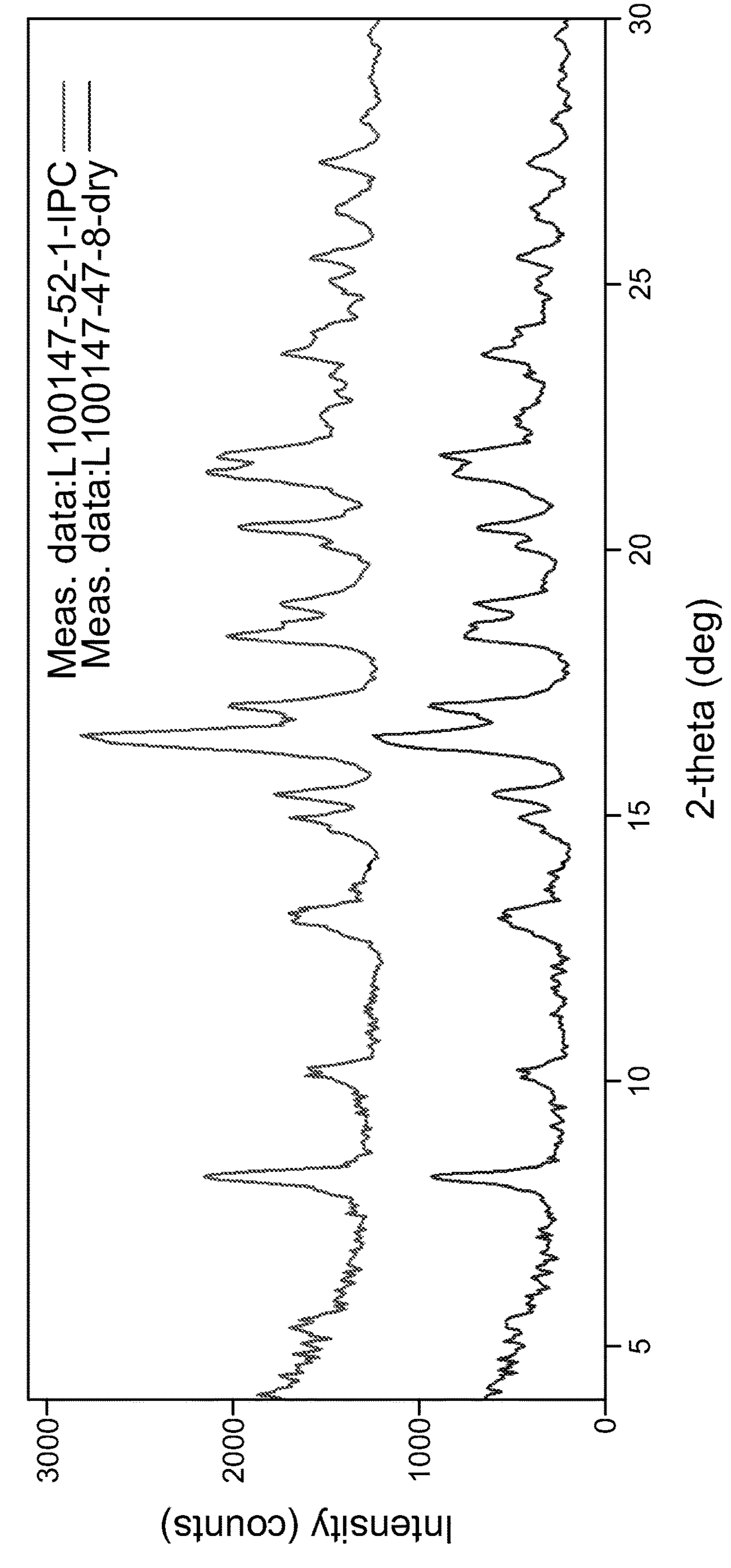
FIG. 21 shows the XRPD patterns of anhydrous 1:1 Compound (I) crystalline HCl salt (Form I) observed during initial screening (bottom) and scaled-up (top).

The X-ray Powder Diffraction (XRPD) patterns of anhydrous 1:1 Compound (I) crystalline HCl salt (Form I) is shown in FIG. 21.

A Form I sample partially converted to Form A overnight in a high humidity environment (>90% RH).

TABLE 10

Peak list for XRPD pattern of Anhydrous 1:1 Compound (I) Crystalline HCl Salt (Form I).

| 2θ (degrees) | d-spacing (angstrom) | Relative Intensity (%) |
|---|---|---|
| 5.44 | 16.23 | 52 |
| 8.22 | 10.75 | 60 |
| 10.21 | 8.66 | 37 |
| 13.06 | 6.77 | 51 |
| 14.94 | 5.92 | 23 |
| 15.40 | 5.75 | 25 |
| 16.33 | 5.42 | 100 |
| 16.51 | 5.37 | 57 |
| 17.05 | 5.19 | 30 |
| 18.35 | 4.83 | 57 |
| 18.98 | 4.67 | 22 |
| 20.05 | 4.43 | 9 |
| 20.42 | 4.34 | 28 |
| 21.49 | 4.13 | 65 |
| 21.78 | 4.08 | 43 |
| 22.49 | 3.95 | 10 |
| 23.70 | 3.75 | 11 |
| 24.10 | 3.69 | 28 |
| 25.00 | 3.56 | 7 |

TABLE 10-continued

| Peak list for XRPD pattern of Anhydrous 1:1 Compound (I) Crystalline HCl Salt (Form I). | | |
|---|---|---|
| 2θ (degrees) | d-spacing (angstrom) | Relative Intensity (%) |
| 25.55 | 3.48 | 12 |
| 26.45 | 3.37 | 10 |
| 27.30 | 3.26 | 12 |
| 30.78 | 2.90 | 5 |
| 34.03 | 2.63 | 14 |
| 35.09 | 2.56 | 4 |
| 35.87 | 2.50 | 11 |

Example 7: Preparations and Characterizations of Anhydrous 1:1 Compound (I) Crystalline Fumarate Salt (Form A)

7.1 Preparations

Figure 27:
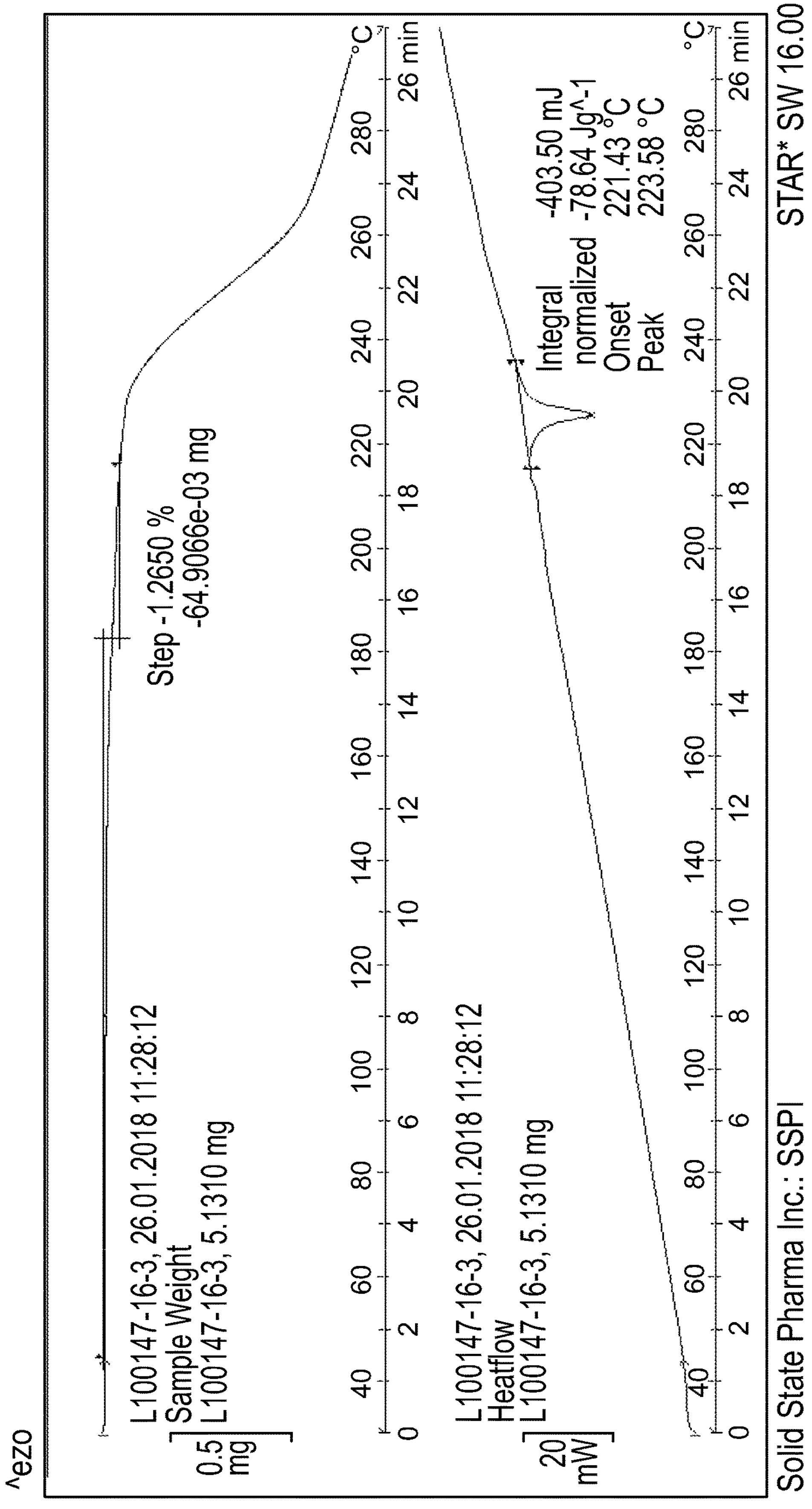
FIG. 27 shows the TGA and DSC thermograms of anhydrous 1:1 Compound (I) crystalline Fumarate salt (Form A).
Figure 28:
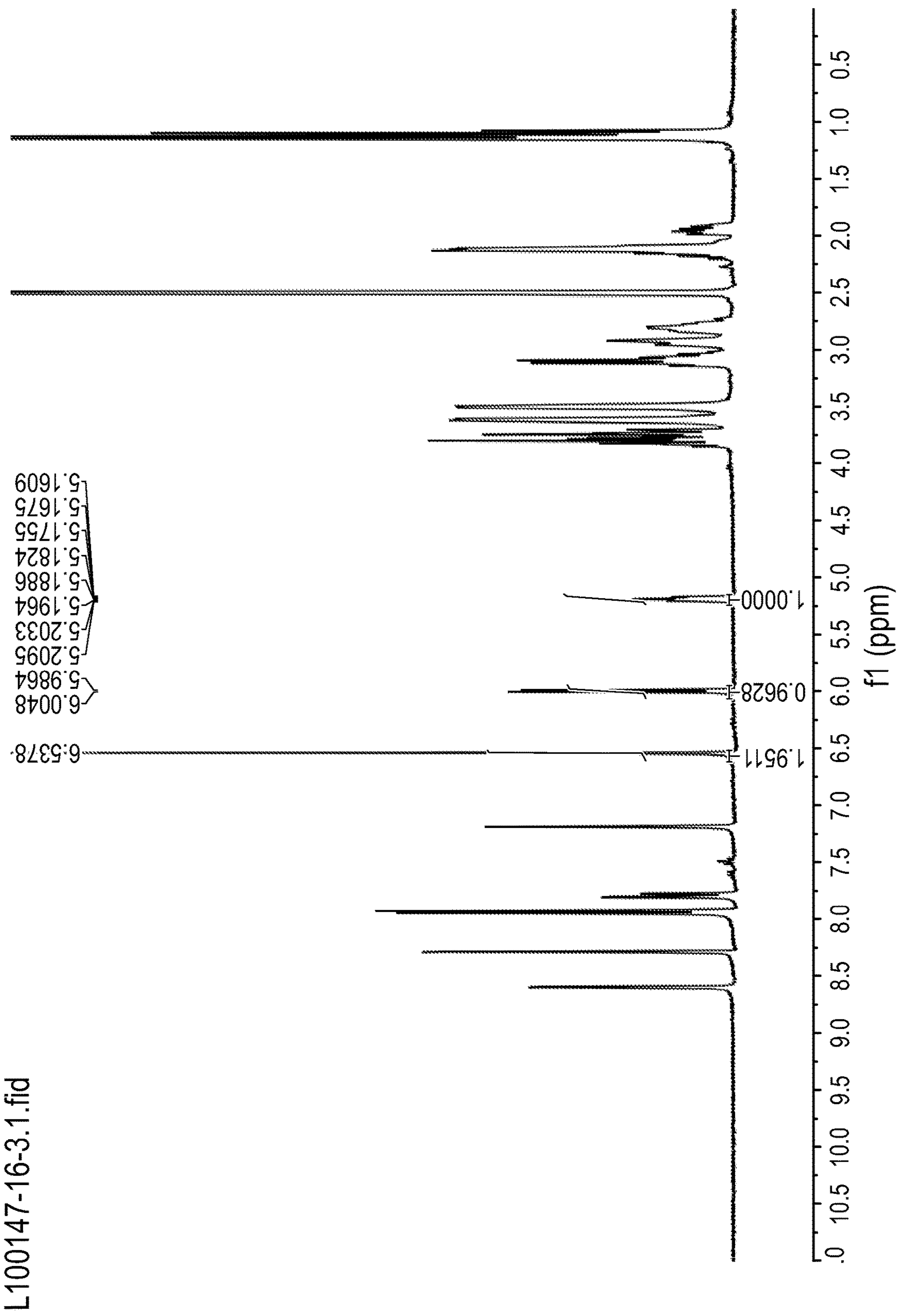
FIG. 28 shows the $^1$H-NMR of anhydrous 1:1 Compound (I) crystalline Fumarate salt (Form A).

Fumarate Form A was scaled-up by weighing freebase of Compound (I) in a 4 mL vial and adding 1.1 equivalents of fumaric acid. EtOAc (15 volumes) was then added at room temperature. Solids mostly dissolved (slurry became very thin) and then solids precipitated forming a thick white slurry. An additional 5 volumes EtOAc was added to improve mixing. The slurry was heated to 45° C. and held for two hours while stirring followed by cooling naturally to room temperature. The slurry was stirred at room temperature overnight. Prior to filtration the slurry was a thick white slurry. The slurry was filtered and washed twice with 2 volumes EtOAc then dried at 50° C. under vacuum overnight. The solid obtained was further characterized by XRPD (see FIG. 26 and Table 11), TGA-DSC (FIG. 27), $^1$H NMR (FIG. 28).

TABLE 11

| Peak list for XRPD pattern of Anhydrous 1:1 Compound (I) Crystalline Fumarate Salt (Form A) | | |
|---|---|---|
| 2θ (degrees) | d-spacing (angstrom) | Relative Intensity (%) |
| 5.72 | 15.45 | 100 |
| 7.54 | 11.72 | 28 |
| 9.76 | 9.05 | 24 |
| 10.29 | 8.59 | 28 |
| 11.21 | 7.89 | 15 |
| 12.25 | 7.22 | 30 |
| 14.79 | 5.99 | 21 |
| 15.25 | 5.80 | 74 |
| 16.21 | 5.46 | 13 |
| 16.86 | 5.25 | 90 |
| 17.16 | 5.16 | 28 |
| 17.52 | 5.06 | 42 |
| 18.26 | 4.86 | 23 |
| 18.78 | 4.72 | 17 |
| 19.87 | 4.47 | 24 |
| 20.66 | 4.30 | 14 |
| 21.46 | 4.14 | 5 |
| 22.39 | 3.97 | 51 |
| 23.04 | 3.87 | 50 |
| 23.49 | 3.78 | 8 |
| 25.79 | 3.45 | 29 |

Example 8: Preparations and Characterizations of Anhydrous 1:1 Compound (I) Crystalline Fumarate Salt (Form C)

8.1 Preparations

Freebase of Compound (I) in a 4 mL vial was added 1.1 equivalents of fumaric acid. IPAc (15 volumes) was then added at room temperature. Solids mostly dissolved (slurry became very thin) and then solids precipitated as an off-white slurry. The slurry was heated to 45° C. and held for two hours while stirring followed by cooling naturally to room temperature. The slurry was stirred at room temperature overnight. Prior to filtration the slurry was a thick white slurry. The slurry was filtered and washed twice with 2 volumes IPAc then dried at 50° C. under vacuum overnight. The solid obtained was further slurried in EtOH and EtOAc and characterized by XRPD (see FIG. 29 and Table 12).

TABLE 12

| Peak list for XRPD pattern of Anhydrous 1:1 Compound (I) Crystalline Fumarate Salt (Form C) | | |
|---|---|---|
| 2θ (degrees) | d-spacing (angstrom) | Relative Intensity (%) |
| 4.45 | 19.82 | 41 |
| 6.30 | 14.02 | 48 |
| 7.41 | 11.91 | 16 |
| 8.96 | 9.86 | 76 |
| 13.50 | 6.55 | 75 |
| 14.68 | 6.03 | 32 |
| 16.24 | 5.45 | 10 |
| 16.78 | 5.28 | 20 |
| 17.35 | 5.11 | 13 |
| 17.78 | 4.98 | 8 |
| 18.36 | 4.83 | 15 |
| 18.92 | 4.69 | 100 |
| 19.65 | 4.52 | 43 |
| 21.04 | 4.22 | 54 |
| 22.50 | 3.95 | 72 |
| 23.63 | 3.76 | 40 |
| 25.46 | 3.50 | 16 |
| 26.22 | 3.40 | 13 |
| 27.51 | 3.24 | 22 |
| 28.31 | 3.15 | 13 |

Example 9: Preparations and Characterizations of Anhydrous 1:1 Compound (I) Crystalline Fumarate Salt (Form D)

9.1 Preparations

Freebase of Compound (I) in a 4 mL vial was added 1.1 equivalents of fumaric acid. IPAc (15 volumes) was then added at room temperature. Solids mostly dissolved (slurry became very thin) and then solids precipitated as an off-white slurry. The slurry was heated to 45° C. and held for two hours while stirring followed by cooling naturally to room temperature. The slurry was stirred at room temperature overnight. Prior to filtration the slurry was a thick white slurry. The slurry was filtered and washed twice with 2 volumes IPAc then dried at 50° C. under vacuum overnight. The solid obtained was further slurried in a mixture of IPA:water (95:5 vol) and characterized by XRPD (see FIG. 30 and Table 13).

TABLE 13

| Peak list for XRPD pattern of Anhydrous 1:1 Compound (I) Crystalline Fumarate Salt (Form D) | | |
|---|---|---|
| 2θ (degrees) | d-spacing (angstrom) | Relative Intensity (%) |
| 4.62 | 19.10 | 100 |
| 10.98 | 8.05 | 26 |
| 11.94 | 7.41 | 7 |
| 14.25 | 6.21 | 5 |
| 15.08 | 5.87 | 7 |
| 18.45 | 4.80 | 23 |
| 19.40 | 4.57 | 8 |

TABLE 13-continued

| Peak list for XRPD pattern of Anhydrous 1:1 Compound (I) Crystalline Fumarate Salt (Form D) | | |
|---|---|---|
| 2θ (degrees) | d-spacing (angstrom) | Relative Intensity (%) |
| 20.48 | 4.33 | 9 |
| 20.98 | 4.23 | 8 |
| 22.78 | 3.90 | 6 |
| 23.62 | 3.76 | 5 |
| 24.97 | 3.56 | 7 |

The invention claimed is:

1. A succinate salt of Compound (I) represented by the following structural formula:

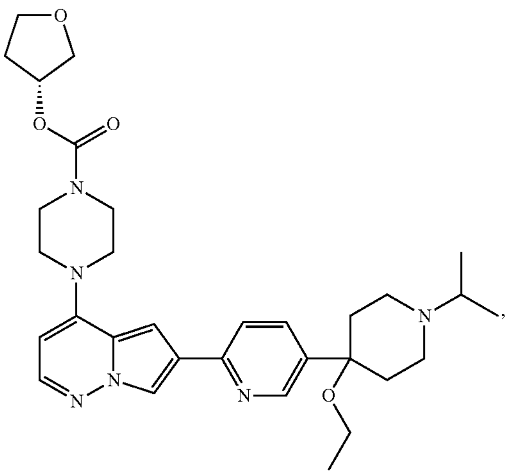

(I)

wherein the molar ratio between Compound (I) and succinic acid is 1:1.5.

2. The succinate salt of claim 1, wherein the succinate salt is crystalline.

3. The succinate salt of claim 1, wherein the succinate salt is in a single crystalline form.

4. The succinate salt of claim 1, wherein the succinate salt is unsolvated.

5. The succinate salt of claim 1, wherein the succinate salt is in a single crystalline form, Form A, characterized by an X-ray powder diffraction pattern which comprises peaks at 8.5°, 15.4°, and 21.3°±0.2 in 2θ.

6. The succinate salt of claim 1, wherein the succinate salt is in a single crystalline form, Form A, characterized by an X-ray powder diffraction pattern which comprises at least three peaks chosen from 4.3°, 8.5°, 14.0°, 15.4°, and 21.3°±0.2 in 2θ.

7. The succinate salt of claim 1, wherein the succinate salt is in a single crystalline form, Form A, characterized by an X-ray powder diffraction pattern which comprises peaks at 4.3°, 8.5°, 14.0°, 15.4°, and 21.3°±0.2 in 2θ.

8. The succinate salt of claim 1, wherein the succinate salt is in a single crystalline form, Form A, characterized by an X-ray powder diffraction pattern which comprises peaks at 4.3°, 6.7°, 8.5°, 12.8°, 14.0°, 15.4°, 17.0°, and 21.3°±0.2 in 2θ.

9. The succinate salt of claim 1, wherein the succinate salt is in a single crystalline form, Form A, characterized by an X-ray powder diffraction pattern which comprises peaks at 4.3°, 6.7°, 8.5°, 12.8°, 14.0°, 15.4°, 15.7°, 16.6°, 17.0°, 18.1°, 19.4°, 19.8°, 20.1°, 20.7°, 21.3°, 22.3°, 25.0°, 29.1°, and 34.4°±0.2 in 2θ.

10. A hydrochloride salt of Compound (I) represented by the following structural formula:

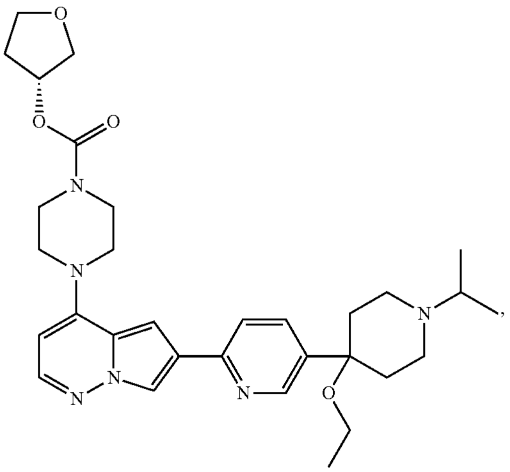

(I)

wherein the molar ratio between Compound (I) and hydrochloric acid is 1:1.

11. The hydrochloride salt of claim 10, wherein the hydrochloride salt is in a single crystalline form, Form A, characterized by an X-ray powder diffraction pattern which comprises at least three peaks chosen from 12.9°, 17.0°, 19.0°, 21.1°, and 22.8°±0.2 in 2θ.

12. The hydrochloride salt of claim 10, wherein the hydrochloride salt is in a single crystalline form, Form I, characterized by an X-ray powder diffraction pattern which comprises at least three peaks chosen from 5.4°, 8.2°, 16.3°, 16.5°, 18.4°, and 21.5°±0.2 in 2θ.

13. A fumarate salt of Compound (I) represented by the following structural formula:

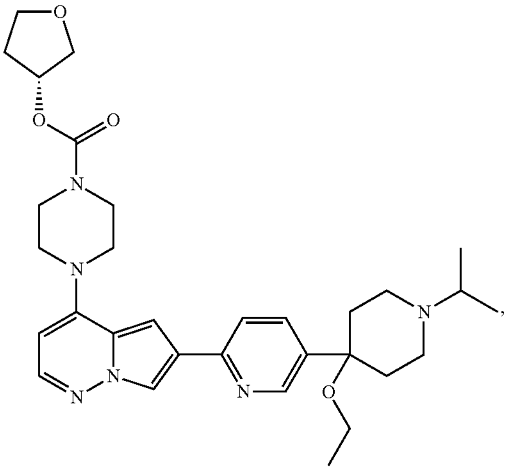

(I)

wherein the molar ratio between Compound (I) and fumaric acid is 1:1.

14. The fumarate salt of claim 13, wherein the fumarate salt is in a single crystalline form, Form A, characterized by an X-ray powder diffraction pattern which comprises at least three peaks chosen from 5.7°, 15.3°, 16.9°, 22.4°, and 23.0°±0.2 in 2θ.

15. The fumarate salt of claim 13, wherein the fumarate salt is in a single crystalline form, Form C, characterized by an X-ray powder diffraction pattern which comprises at least three peaks chosen from 6.3°, 9.0°, 13.5°, 18.9°, and 22.5°±0.2 in 2θ.

16. The fumarate salt of claim 13, wherein the fumarate salt is in a single crystalline form, Form D, characterized by an X-ray powder diffraction pattern which comprises at least three peaks chosen from 4.6°, 11.0°, 18.5°, 20.5°, and 21.0°±0.2 in 2θ.

17. A pharmaceutical composition comprising the salt of claim 1, and a pharmaceutically acceptable carrier or diluent.

18. A method of treating or ameliorating fibrodysplasia ossificans progressiva in a subject, comprising administering to the subject in need thereof a pharmaceutically effective amount of the salt of claim 1.

19. A method of treating or ameliorating diffuse intrinsic pontine glioma in a subject, comprising administering to the subject in need thereof a pharmaceutically effective amount of the compound of claim 1.

20. A method of inhibiting aberrant ALK2 activity in a subject comprising the step of administering to the subject in need thereof a pharmaceutically effective amount of the compound of claim 1.

21. The succinate salt of claim 5, wherein the succinate salt is in a single crystalline form, Form A, characterized by a differential scanning calorimeter (DSC) peak phase transition temperature of 177±2° C.

* * * * *